United States Patent [19]

Ichimura et al.

[11] Patent Number: 5,249,072
[45] Date of Patent: Sep. 28, 1993

[54] HETERODYNE RECEPTOR SYSTEM AND ARRANGEMENT FOR VISUALIZING OPTICAL TRANSMISSION IMAGES

[75] Inventors: Tsutomu Ichimura; Fumio Inaba; Masahiro Toida, all of Sendai, Japan

[73] Assignee: Research Development Corporation of Japan, Tokyo, Japan

[21] Appl. No.: 689,883
[22] PCT Filed: May 30, 1990
[86] PCT No.: PCT/JP90/00694
   § 371 Date: May 24, 1991
   § 102(e) Date: May 24, 1991
[87] PCT Pub. No.: WO91/05239
   PCT Pub. Date: Apr. 18, 1991

[30] Foreign Application Priority Data

Sep. 26, 1989 [JP] Japan .................. 1-250036

[51] Int. Cl.$^5$ .............. H04B 10/06; G01B 9/02
[52] U.S. Cl. ..................... 359/191; 356/349; 359/193; 359/561
[58] Field of Search .............. 359/10, 11, 29, 560, 359/561, 191, 193; 356/337, 343, 349; 351/206

[56] References Cited

U.S. PATENT DOCUMENTS

| | | |
|---|---|---|
| 4,193,088 | 3/1980 | Moran . |
| 4,195,221 | 3/1980 | Moran . |
| 4,242,194 | 12/1980 | Steiner et al. .............. 356/337 |
| 4,305,666 | 12/1981 | Becherer et al. .............. 356/349 |
| 4,442,455 | 4/1984 | Huignard et al. .............. 356/349 |
| 4,707,135 | 11/1987 | Swain et al. .............. 356/349 |
| 4,820,047 | 4/1989 | Snyder .............. 356/349 |
| 4,907,886 | 3/1990 | Dandliker .............. 356/349 |
| 4,909,628 | 3/1990 | Aoshima et al. .............. 356/349 |
| 4,950,070 | 8/1990 | Aizu et al. .............. 351/206 |
| 4,952,050 | 8/1990 | Aizu et al. .............. 351/206 |
| 4,955,974 | 9/1990 | Rhodes et al. .............. 359/10 |
| 5,014,709 | 5/1991 | Bjelkhagen et al. .............. 359/10 |
| 5,052,806 | 10/1991 | Snyder .............. 356/343 |

FOREIGN PATENT DOCUMENTS 3-17535 1/1991 Japan .................. 356/349

*Primary Examiner*—Martin Lerner
*Attorney, Agent, or Firm*—Armstrong, Westerman, Hattori, McLeland & Naughton

[57] ABSTRACT

The present invention provides a receptor system in which laser light from a laser source is directed onto a sample, the transmitted light from which is photomixed by a half mirror with laser light different in frequency from laser light from a local oscillator source, and the photomixed light is received by a receptor element dividing a light propagating zone into a plurality of sub-zones, said receptor element having an exit end, at which a spatial zone, which is defined between different points and in which interference occurs, is limited within a spatially resolvable minimum unit, to form a Fraunhofer diffraction image, whereby the 0 order diffraction image of the Fraunhofer diffraction image is partly or wholly detected by a photodetector, or alternatively a diffraction image at most n times as large as the 0 order spectrum is detected by the photodetector. By extracting a beat component from the photomixed light in this manner, a transmission image can be separated from scattered components for detection. With light including too many scattered components such as that transmitted through the human body or the like, it is possible to obtain information relating to an absorber. This invention is thus applicable to optical computer tomography, etc.

12 Claims, 19 Drawing Sheets

FIG. 3

| | ROUND APERTURE $\frac{2J_1(X_1)}{X_1}$ | RECTANGLAR APERTURE $\frac{\sin X_1}{X_1}$ | ANNULAR APERTURE $J_0(X_1)$ |
|---|---|---|---|
| ROUND APERTURE $\frac{2J_1(X_2)}{X_2}$ | $\frac{2J_1(X_1)}{X_1} \cdot \frac{2J_1(X_2)}{X_2}$ | $\frac{\sin X_1}{X_1} \cdot \frac{2J_1(X_2)}{X_2}$ | $J_0(X_1) \cdot \frac{2J_1(X_2)}{X_2}$ |
| RECTANGLAR APERTURE $\frac{\sin X_2}{X_2}$ | $\frac{2J_1(X_1)}{X_1} \cdot \frac{\sin X_2}{X_2}$ | $\frac{\sin X_1}{X_1} \cdot \frac{\sin X_2}{X_2}$ | $J_0(X_1) \cdot \frac{\sin X_2}{X_2}$ |
| ANNULAR APERTURE $J_0(X_2)$ | $\frac{2J_1(X_1)}{X_1} \cdot J_0(X_2)$ | $\frac{\sin X_1}{X_1} \cdot J_0(X_2)$ | $J_0(X_1) \cdot J_0(X_2)$ |

Top-left cell: DIFFRACTION IMAGE OF LOCAL OSCILLATOR LIGHT / DIFFRACTION IMAGE OF RECEIVED LIGHT FIG. 30(a)
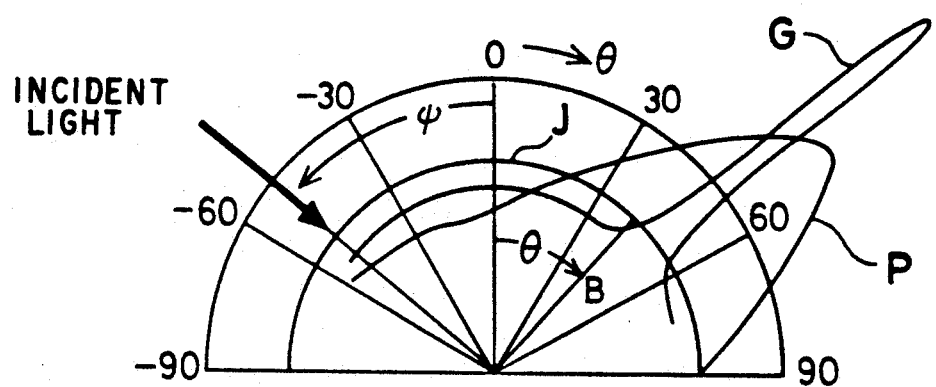
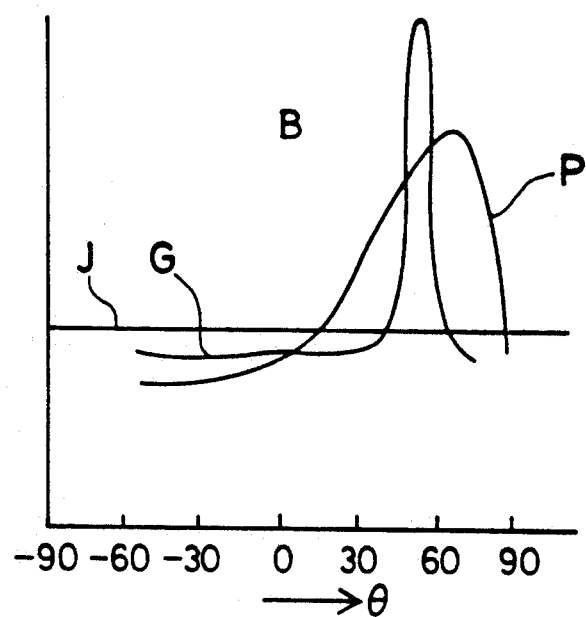
FIG. 30(b)

HETERODYNE RECEPTOR SYSTEM AND ARRANGEMENT FOR VISUALIZING OPTICAL TRANSMISSION IMAGES

TECHNICAL FIELD

This invention relates to a heterodyne receptor system capable of detecting with high resolution information light buried in scattered light and an arrangement capable of visualizing optical transmission images.

BACKGROUND TECHNIQUE

When light scatterers like biological tissues are illuminated with light, the resulting, rectilinearly propagating light could be extracted to some extent in a 180° face-to-face system. As yet, however, the spatial resolving power is not good enough.

A difference in the spatial resolving power between light and X-rays cannot be made up for as yet. The use of light, esp. near infrared rays, however, will be able to construct images of tissue's oxygen concentrations from hemoglobin in the blood. These will provide information different from that obtained with other techniques such as Now let us assume an object 0 shown in FIG. 22 does not contain too much scatterers and is relatively close to transparency. Then, light having a specific wavelength component selected through a filter 340 is directed onto the object 0 from a ring type of slit 341 placed at the focal position of a lens $L_1$, so that the enlarged image can be focused onto a plane P through an objective $L_2$ for observation. The use of the ring type of slit 341 located at the focal point of the lens $L_1$ is tantamount to irradiating the object 0 with light in every direction, as shown in FIG. 23, so that images $I_1$, $I_2$, and so on, of the object 0 in the respective directions can be observed at once.

Given a 3 to 5-cm thick tissue, we can detect light transmitted through it. This means that "opto-radiography" can be used for diagnosis. The mammas are relatively uniform in tissue and easy to transmit light, and the transmitted light is easily detectable (at a thickness up to about 3 cm) because of their form. Thus, this technique has long been used for the diagnosis of breast cancer under the name of "Diaphanography" or "Lightscanning". One such conventional diagnostic system will now be explained with reference to FIG. 24.

The construction of a conventional system for obtaining a light absorption distribution image is illustrated in FIG. 24, wherein reference numeral 401 stands for a scan head, 403 the human body, 405 a video camera, 407 an A/D converter, 409 a near infrared light frame memory, 411 a red light frame memory, 413 a processor, 415 a color conversion processor, 417 an encoder keyboard, 419 a D/A converter, 412 a printer, 423 a TV monitor and 425 a video tape recorder. The spot of the human body to be inspected, e.g. the mamma is irradiated and scanned alternately with red light (strongly absorbed in hemoglobin in the blood in particular) and near infrared light (absorbed in the blood, fluids, fat, etc.) by the scan head 401 through a light guide. As shown, the spot is illuminated with light from below. As a result, the mamma glows brightly, and the transmission image is picked up by the video camera 401. That image is converted through the A/D convertor 407 into digital signals, and the near infrared light and red light are fed in the frame memories 409 and 411, respectively, through a digital switch. The ratio of intensities of near infrared light and red light is then computed in the processor 413, and is further converted into analog signals by color conversion processing. The resulting light absorption distribution image is finally observed through a printer, a TV monitor or a video tape.

This system's resolving power is not good enough, because the light leaving the scan head 401, which is not parallel light, diverges through the tissue (the mamma), as much it would be illuminated with the light from a flashlight, and is received by such a two-dimensional receptor as a video camera.

An example of conventional illuminator/receptor systems collimated so as to make improvement in this regard will now be explained with reference to FIG. 25.

FIG. 25 is a diagrammatic sketch illustrating the construction of a conventional unit for obtaining light absorption distribution images using a collimated illuminator/receptor system.

In this example, laser light emanating from a light source is guided onto an object 435 to be inspected through an optical fiber 433 for illumination, and the transmitted light is picked up by a fiber collimator 437 and fed into a receptor 443 wherein it is converted into electrical signals, which are in turn processed in a computer 451 through a preprocessing circuit 445, an A/D converter 447 and an interface 449. In this case, scanning is carried out while the optical fibers 433 for illumination are synchronized with the fiber collimator 437 for detection by a motor 439, thereby obtaining light absorption distribution images of the respective spots of the object, which are in turn observed on a monitor 453.

It is noted that the red light source used is a 633-nm He-Ne laser and the near infrared light source used an 830-nm semiconductor laser. With this diagnostic unit, Jobsis and coworkers reported in 1977 that they succeeded in detecting light transmitted through the heads of cats or humans illuminated with near infrared light and the amount of that transmitted light was found to vary depending upon the animals' respiration. With near infrared light having a wavelength of 700 to 1500 nm and a tissue specimen, nearly the size of the head of a cat, the transmitted light could be well detected at a dose of about 5 mill. This dose is greatly safe, because it is about 1/50 or less of the present safety standards for laser, or about 1/10 of near infrared light to which we are now being exposed at the seaside.

Incidentally, when living bodies, etc. are irradiated with light, the transmitted light is absorbed and scattered by the specimens.

FIG. 26 is the Twersky's scattering theory curves that clarifies the relationship between the absorbance of an erythrocite-suspending fluid and the concentration of hematocrit, and shows the intensity, scattered and absorbance components of the transmitted light obtained by illumination of laser light having a wavelength of 940 nm.

As can be seen from FIG. 26, the transmitted light has the large scattered component superposed on the absorbance component. The scattered component, because of being directionality-free, has the property of coming to contain scattered light from various spots and making optical tomograms blurry. For this reason, mere detection of the transmitted light does not allow the absorbance component, that is the required information, to be detected with high accuracy.

FIG. 27 is a diagrammatic sketch illustrating the optical properties of such a specimen as a living body.

Referring here back to FIG. 22, the object O contains no scattering component. In other words, what is observed in FIG. 22 is, so to speak, an originally visible object. A specimen 460 of FIG. 27, that is to be actually observed, should be essentially considered to be made up of a Rayleigh scatterer 460a smaller than the wavelength of light; a Mie scatterer 460b nearly the size of the wavelength of light; a light transmission information carrier 460c that is the target to be observed and absorbs light; a diffuser 460d that diffuses light; a diffraction grating 460e that gives rise to random diffraction; and so on. When such a specimen is irradiated with coherent plane waves through a laser optical system 461, light leaving it comes to contain, in addition to the transmitted light, the Rayleigh scattered, Mie scattered, diffused, randomly diffracted and other forms of light. So far, it has been impossible to detect only the light transmitted through the information carrier 460c from all such forms of light.

FIG. 28 is a diagrammatic sketch illustrating a Fresnel diffraction wave produced by a sinusoidal grating having a finite aperture.

As a plane wave is directed onto the finite aperture, side bands 471 and 472 occur in addition to transmitted light 470. With a random diffraction grating, therefore, difficulty will be involved in detecting and observing the transmitted light with high sensitivity owing to the influence of the side bands.

FIGS. 29A and 29B are diagrammatic sketches illustrating a luminance distribution found on a plane of view located in opposition to a random scatterer, when it is illuminated with coherent light.

When such a scatterer as a living body is irradiated with such coherent light as laser light, a random diffraction image appears on the plane of view, as shown in FIG. 29a. Then, the transmitted light through the scatterer is focused by a lens L onto the plane of view, as shown in FIG. 29b. However, it is impossible to inspect an image of the spot of a living body or the like to be observed with high resolution, because a random diffraction image is superposed on that image.

FIGS. 30A and 30B are diagrammatic sketches showing a luminance distribution of reflected light that depends on what state a diffuse reflection plane is in, with FIGS. 30a and 30b taking the form of polar and rectangular coordinates, respectively.

In FIGS. 30A and 30B, J stands for a luminance distribution of light reflected from a perfect diffusion plane, G denotes a luminance distribution of light reflected from a glossy plane, and P indicates a luminance distribution of light reflected from a dim plane. On the glossy plane the luminance distribution shows a peak converging sharply in the predetermined direction, while on the dim plane the luminance distribution is diverging. Thus, it turns out that the luminance distribution varies depending upon what state the plane is in and that the accuracy of observation making use of reflected light is largely governed by what state the plane is in.

As mentioned above, if tomographic images are observed with coherent light, it is then impossible to view them with high resolution, since the required information light is buried in various forms of scattered light.

Having been accomplished with a view to providing a solution to the above-mentioned problems, the present invention has for its object to provide a heterodyne receptor system capable of detecting the required information light from many scattered components with the use of a short receptor element, even when information light is buried therein, whereby optical tomograms of a living body or the like can be imaged, and an arrangement for imaging optical tomograms.

DISCLOSURE OF THE INVENTION

According to one aspect of this invention, there is provided a heterodyne receptor system characterized by including laser light transmitted through a sample, mixing means for mixing said laser light with another laser light having a frequency different from that of said laser light, a receptor element which the resulting light enters and divides a light propagating zone into a plurality of sub-zones and a detector for detecting a beat component of the mixed light out of light leaving said receptor element, said receptor element having an exit end, at which a spatial zone, which is defined between different points and in which interference occurs, is limited within a spatially resolvable minimum unit to detect the beat component of the mixed light.

According to another aspect of this invention, there is provided an arrangement for visualizing optical transmission images, characterized by including a stage for moving a sample, means for directing one of two laser beams with a given frequency difference therebetween onto said sample and mixing the transmitted light with the other laser light, a receptor element which the resulting light enters and include a plurality of divided, light propagating zones and a detector for detecting a beat component of the mixed light out of light leaving said receptor element, means for computing the detected signals, and means for displaying the result of said computing, whereby a beat component is extracted from light leaving said sample to visualize an optical transmission image.

According to this invention, laser light transmitted through a sample is mixed with laser light different in frequency therefrom, and the resulting light is received by a receptor element which divides a light propagating zone into a plurality of sub-zones, each of said sub-zones being limited within a spatially resolvable minimum unit in which interference occurs between different points, thereby forming a Fraunhofer diffraction image to detect the n order diffraction images at most. This is because it is difficult to extract the 0 order diffraction image alone when the magnitude of the 0 order Fraunhofer diffraction image is no more than 1 mm. For this reason, the size of a pinhole through which diffraction images are extracted is fixed on the mm order, on which an misalignment of an optical system due to vibration or fluctuation is negligible, thereby extracting a spectrum at most n times the 0 order light. Then, the beat component is extracted from the mixed light to separate a transmission image from scattered components for detection.

BRIEF DESCRIPTION OF THE DRAWINGS

FIG. 3 is a table illustrating the principle on which heterodyning according to this invention is based, FIGS. 4, 5A, and 5B each are a diagrammatic sketch illustrating the principle of how to form an image, FIGS. 30A and 30B are diagrammatic sketches illustrating a reflection pattern on a diffuser plane.

DETAILED DESCRIPTION OF THE INVENTION

Figure 4:
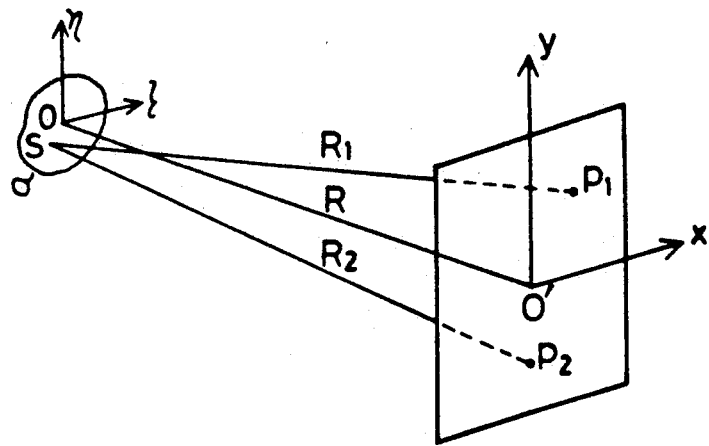

Reference will now be made to the fundamental principle of this invention. This invention is based on the so-called van Cittert-Zernike therorem that, as shown in FIG. 4, the degree (or the complex factor) of coherence—which describes the correlation of vibration between a fixed point $P_2$ and a mobile point $P_1$ on a plane illuminated with light from a quasimonochromatic, primary light source $\sigma$ of finite dimensions—is equal to the normalized complex amplitude on the corresponding point $P_1$ in a diffraction image around the point $P_2$, and that this diffraction image is formed when that light source is replaced by a diffraction hole identical in size and form with it and its aperture is converged into $P_2$, so that the wavefront amplitude is met by a spherical wave proportional to the intensity of the light source. The image formation equation is derived on the basis of this theorem.

Figure 5A:
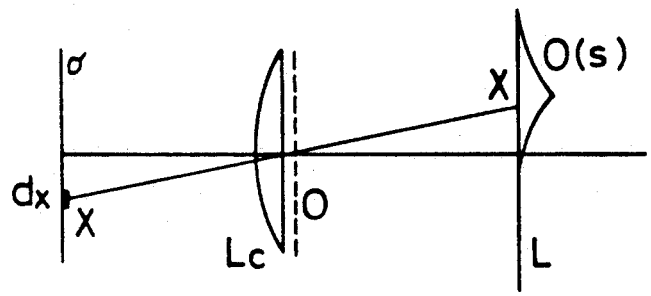
Figure 5B:
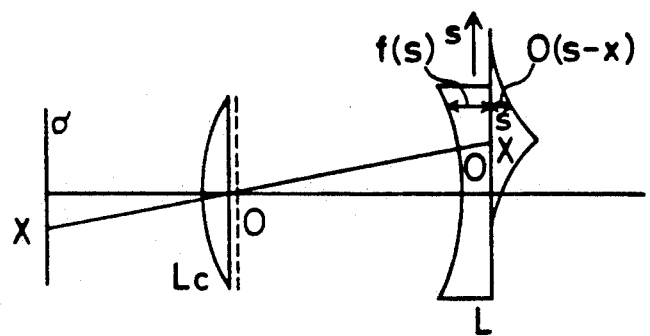

Now let us consider an image in a projection optical system which, for simplicity, may be dealt with two-dimensionally. As shown in FIG. 5a, assume that light from a minuscule light source dx located at a point X on a plane $\sigma$ is coherent and passes through a lens Lc and an object 0 to form a spectrum O(s) on a plane L, the center (0 frequency) of which is found at X. Since $\sigma$ and L are shown on the same coordinates X on which the origin of O(s) is found, the component capable of passing through L is a portion of that. As illustrated in FIG. 5a, the pupil function f is then given by $$f(s) = a(s) e^{-i(2\pi/\lambda)w(s)} \quad (|s| \leq 1) \tag{1}$$

wherein a(s) and W(s) stand for the absorption and wavefront aberrations of the lens, respectively. It is assumed, however, that the origin of f(s) in Equation (1) is found on the point of intersection of the pupil with the optical axis. Thus, the spectrum capable of passing through f(s) is given by $$O(s-X)f(s)$$

If the intensity of the point X is 1, then the spectrum passing through the pupil is subjected to Fourier inverted transformation by the lens L. In other words, the complex amplitude of the image on the imagewise plane is given by $$o'(u') = \int O(s-x) f(s) e^{2\pi i u's} ds \tag{2}$$

Thus, the intensity produced by dx on the imagewise plane is given by $$i(u')dX = |\int O(s-X)f(s)e^{2\pi i u's} ds|^2 \tag{3}$$

Equation (3) may also be interpreted as follows. That is, the complex amplitude o'(u') of the image on the imagewise plane is given by $$o'(u') = \int_{-\infty}^{+\infty} O(s' - X)f(s') e^{2\pi i u's'} ds' \tag{4}$$

It is noted, however, that the variable s in Equation (4) is changed to s'. It is also understood that although the pupil function is finite, it is otherwise 0 so that the lower and upper limits of integration are fixed at $\pm \infty$.

If $s' - X = f'$ in Equation (4), then $ds' = df'$. Thus, $$o'(u') = \int_{-\infty}^{+\infty} O(f')f(f' + X) e^{2\pi i u'(f'+X)} df' \tag{5}$$

$$= e^{2\pi i u' X} \int_{-\infty}^{+\infty} O(f') \times f(f' + x) e^{2\pi i u' f'} df'$$

Rewriting the variable as s'' and using s''−X=f'', we may rewrite (5) as follows:

$$o'^*(u') = e^{-2\pi i u' x} \int_{-\infty}^{+\infty} O^*(f'') \times f^*(f'' + x) e^{-2\pi i u' f''} df'' \tag{6}$$

wherein o'*(u') is the complex conjugate for o'(u') or $$i(u')dX = o'(u') \, o'^*(u')dX \tag{7}$$

Integration of this with all the effective light source $\sigma(X)$ gives $$I(u') = \int_{-\infty}^{+\infty} \sigma(X)i(u')dX \tag{8}$$

Now, substituted (5) and (6) for (7) and then for (8) gives $$I(u') = \int \sigma(X)dX \int \int O(f') O^*(f'') \times \tag{9}$$
$$f(f' + X)f^*(f'' + X) e^{2\pi i u'(f'-f'')} df'df''$$
$$= \int \int \int \sigma(X)f(f' + X)f^*(f'' + X) \times$$
$$O(f')O^*(f'') e^{2\pi i u'(f'-f'')} df'df''dX$$

Here, separation of the integral calculus containing X gives $$\int \sigma(X)f(f'+X)f^*(f''+X)dX = T(f',f'') \tag{10}$$

This T is called the cross modulation coefficient. Substituting T for (9) gives the following image formation equation:

$$I(u') = \int \int_{-\infty}^{+\infty} T(f',f'')O(f')O^*(f'') \times \tag{11}$$
$$e^{2\pi i u'(f'-f'')} df'df''$$
$$= \int \int_{-\infty}^{+\infty} \sigma(x)f(f' + X)f^*(f'' + x)O(f') \times$$
$$O^*(f'') e^{2\pi i u'(f'-f'')} df'df''dx$$

Equation (11) means that if the object spectrum is expressed as O(s), then the image I(u') is found by integrating the total frequency with respect to the product of the interference fringe formed by a beat between the spectra O(f') and O*(f'') multiplied by the weight T(f', f''). Referring to T(f',f'') that is not a function of f'-f'' alone, f' and f'' vary with position, even when f'-f'' vary with position, even when f'-f'' is constant. Thus, the image formation equation represents a nonlinear mapping system to which the same T(f', f') cannot be applied, generally making image formation analyses difficult, because T(f', f'') varies with f' and f'', even when the beat frequency f'-f'' =f is constant.

Figure 6:
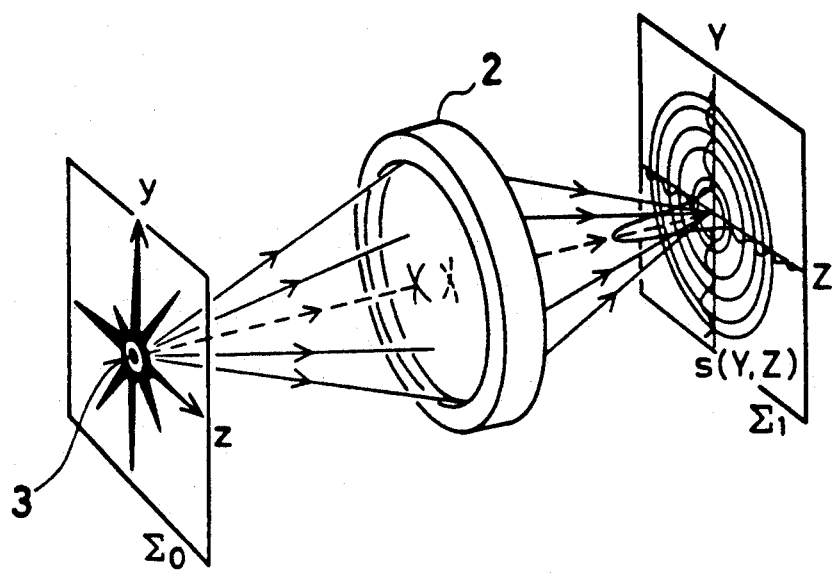
FIG. 6 is a diagrammatic sketch illustrating how to form an image with coherent light.

For instance, consider transmission of light through a minuscule hole 3 in an object plane $\Sigma_o$, as shown in FIG. 6. The light is focused through a lens system 2 onto an image-forming plane $\Sigma_i$ to give a light intensity distribution which spreads around a certain point on that plane in the form of a ring. This means that light beams from the respective points of the object interfere with one another on the image-forming plane. Thus, any imagery analyses cannot be made without integrating all the influences of such interference.

Where a solution of this image formation equation is obtained is:

(a) Incoherent System where $\sigma(x)$ is infinite

Figure 7:
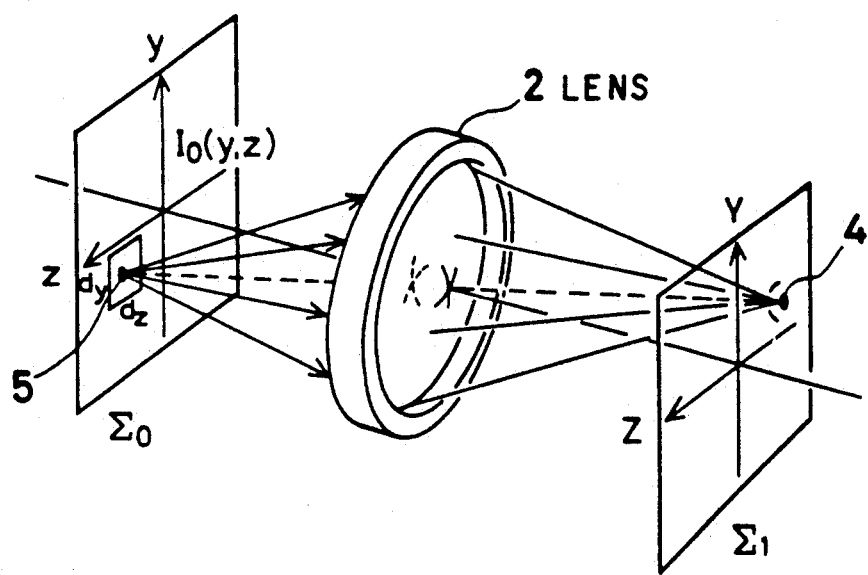
FIG. 7 is a diagrammatic sketch illustrating how to form an image with incoherent light.

T(f', f'') is a function of f=f'-f'' alone and has a linear form. This function T(f) is called a response function. In the case of image formation by incoherent light, the light is directed through a minuscule zone 5 in an object plane $\Sigma_o$ and a lens system 2 onto an image-forming plane $\Sigma_i$ to produce an image on a point 4 thereon, as shown in FIG. 7. In this case, the light intensity on the imagery plane is converged into the point 4, giving a sharp peak. Accordingly, the respective points of the object are imaged on the image-forming plane independently or without interfering with one another.

(b) Coherent System where $\sigma(x)$ is a point source of light

The image formation equation (11) can be reduced because T(f', f')=const. This function T(f) is called a response function.

(c) Approximately Linear System

This is a partially coherent system in which an object is substantially transparent and faint images or minuscule object points are scattered. In that system much of illumination light passes straightforward through the object. Thus, only the zero order spectrum is large in magnitude while other higher order spectra are very small, so that the component of the beat f=f'-f'' can be disregarded, enabling an image to be primarily formed by only the beat components of the spectra f'=0 and f'. Then, since f'=f, the system's mapping characteristics can be approximately described by f alone.

Figure 8A:
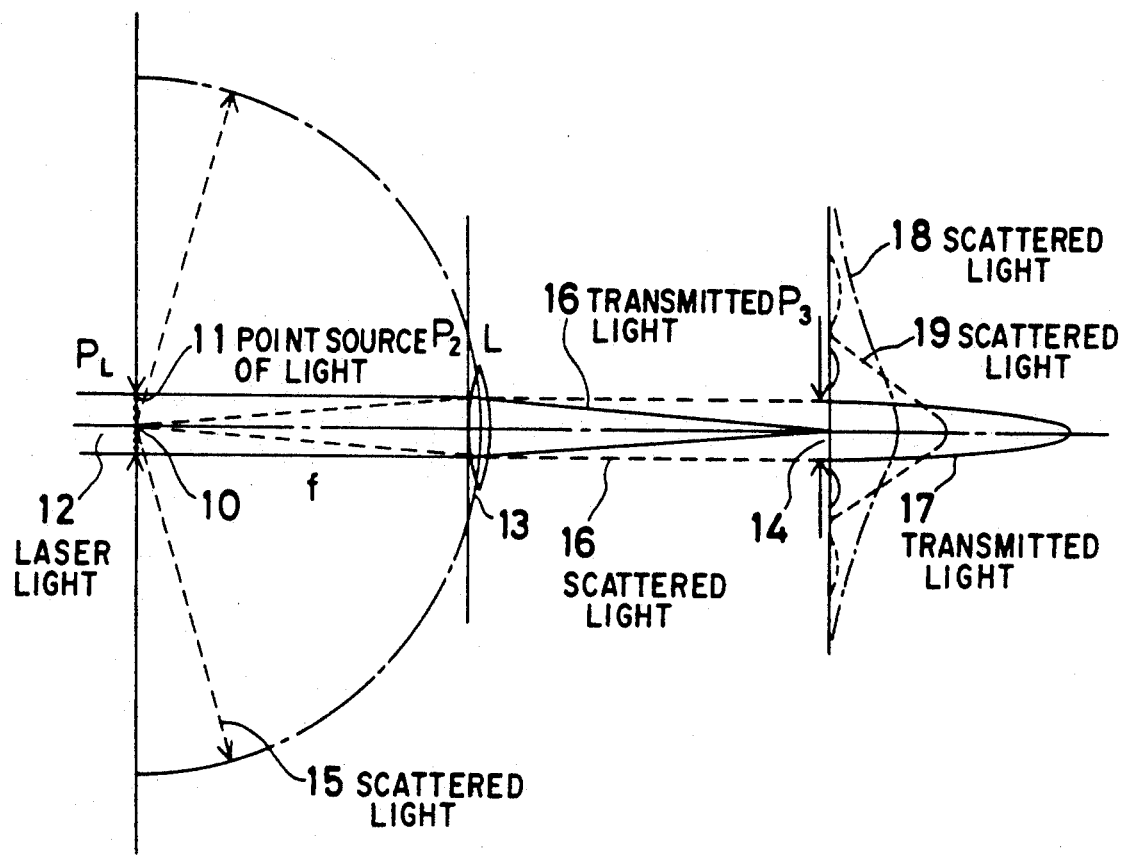
FIGS. 8A and 8B are diagrammatic sketches illustrating Fraunhofer diffraction images formed with plane and spherical waves.
Figure 8B:
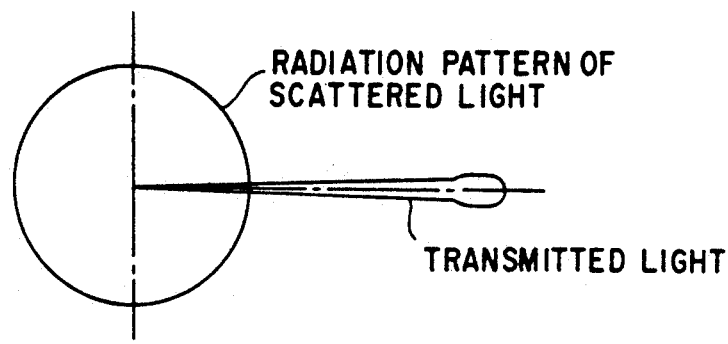

Incidentally, when laser light has been transmitted through an aperture 10 as shown in FIG. 8a, it is considered that in the aperture 10 there are innumerable point sources 11 of light with respect to the scattered light. The transmitted light, on the other hand, diverges in the form of plane diffraction waves that propagate in the same direction as does the incident light. In other words, the radiation pattern of the scattered light takes a spherical form and that of the transmitted light, propagating in the form of plane diffraction waves, is of sharp directionality. On a sufficiently spaced-away plane P3, a Fraunhofer diffraction image is then found. As shown as transmitted light 17, the plane waves show a intensity distribution in which the 0 order spectrum is very large in magnitude but other higher order spectra are small. Scattered light 18 by a gathering of spherical waves, on the other hand, shows a flat form of intensity distribution, as illustrated. When a lens 13 has been placed at an intermediate position in the optical system, however, scattered light 19 also shows a diffraction pattern in which the 0 order spectrum is relatively large in magnitude. At this position at which the Fraunhofer diffraction image is obtained, the scattered light is so attenuated, as can be seen from FIG. 8a, that the 0 order spectrum of the plane wave can be sufficiently increased in magnitude.

For observation of the 0 order diffraction image of a Fraunhofer diffraction image there are two ways, according to one of which it is observed afar off while an aperture is irradiated with plane waves. According to the other technique, it is viewed on the focal plane of a convex lens.

The longer the distance of view, the larger the magnitude of the 0 order diffraction image (a first dark ring of the Airy's disk) of a Fraunhofer diffraction image formed through an aperture (a spatially resolvable minimum unit on an object plane) is proportionally. Thus, it may exceed the aperture in magnitude. Taking the case of using an aperture of several millimeters to a fraction of millimeter in size in combination with an incident wavelength of about 500 nm, however, it is possible to obtain the 0 order diffraction image somewhat smaller than the aperture at the shortest distance at which Fraunhofer diffraction can be observed anyhow.

With a convex lens of several centimeters to a few tens centimeters in focal length and several millimeters to a fraction of millimeter, on the other hand, the 0 order diffraction images of Fruaunhofer diffraction images formed through that lens may be smaller or larger the lens aperture, although this is dependent upon how to combine the focal length with the aperture's size.

Where the magnitude of the Fraunhofer's 0 order diffraction image is no more than the order of millimeter, some difficulty is involved in extracting the 0 order diffraction light alone due to the oscillation of a measuring system or other like factors. For that reason, heterodyning is utilized a means for extracting diffraction images at most n times the 0 order to make separation between scattered light and transmitted light.

Where the Fraunhofer's 0 order diffraction image is no less than the order of a millimeter, on the other hand, heterodyning is again employed as a means for extracting only the 0 order diffraction light wholly or partly to make separation between scattered light and transmitted light. In this connection, it is noted that the heterodyne system designed to extract a portion of the 0 order diffraction light is inferior in the minimum detection sensitivity to that designed to extract the 0 order diffraction light in its entirety.

Figure 9:
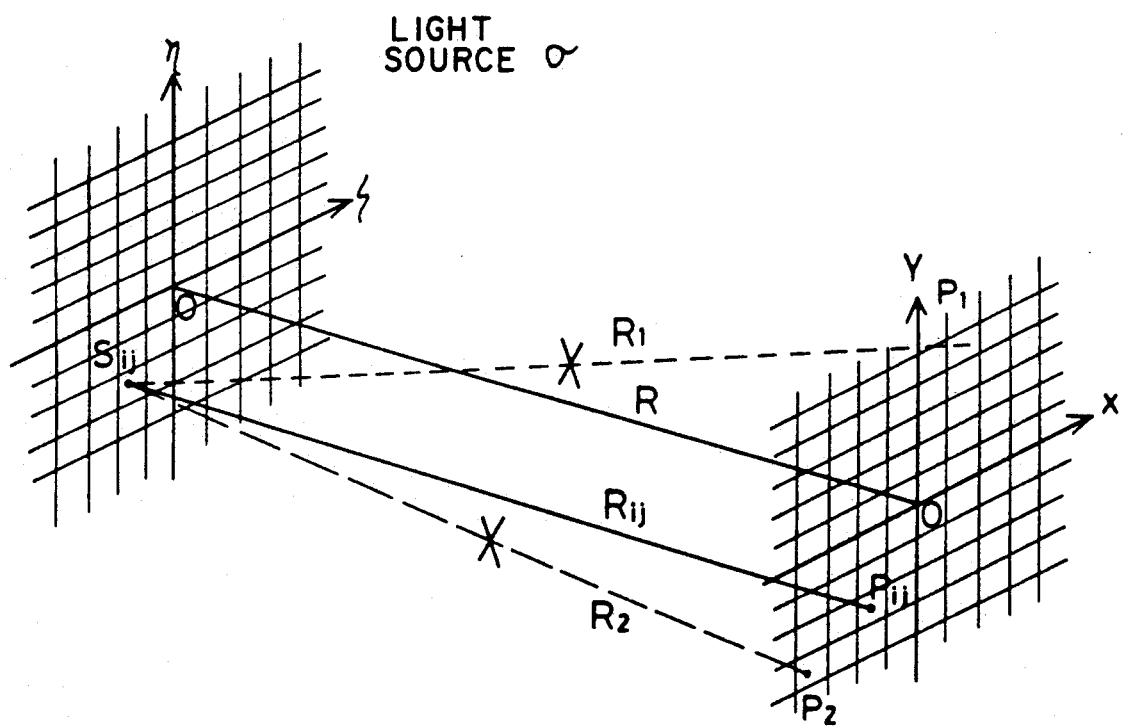
FIG. 9 is a diagrammatic sketch illustrating how to form an image according to this invention.

Now consider the case where the size of the Fraunhofer's 0 order diffraction image is no more than the order of a millimeter. In this case, if only the 0 order spectrum of the Fraunhofer diffraction image is observed as the beat component for heterodyning, it is then possible to glean much information relative to the object of interest—because of its enhanced light intensity—and to get rid of scattered components substantially. In addition, it is possible to linearize the above-mentioned response function and thereby simplify image formation analyses, because the higher order spectra of plane waves are unlikely to have an influence upon other positions. Referring now to FIG. 9, a light source $\sigma$ is spaced away by a distance R from a plane P on which a Fraunhofer diffraction image is observable. The intensity of light from a minuscule light source $S_{ij}$ on the plane P is detected only with respect to $P_{ij}$ in the axial direction corresponding to the source $S_{ij}$, and not with respect to other positions such as $P_1$ and $P_2$.

Figure 10A:
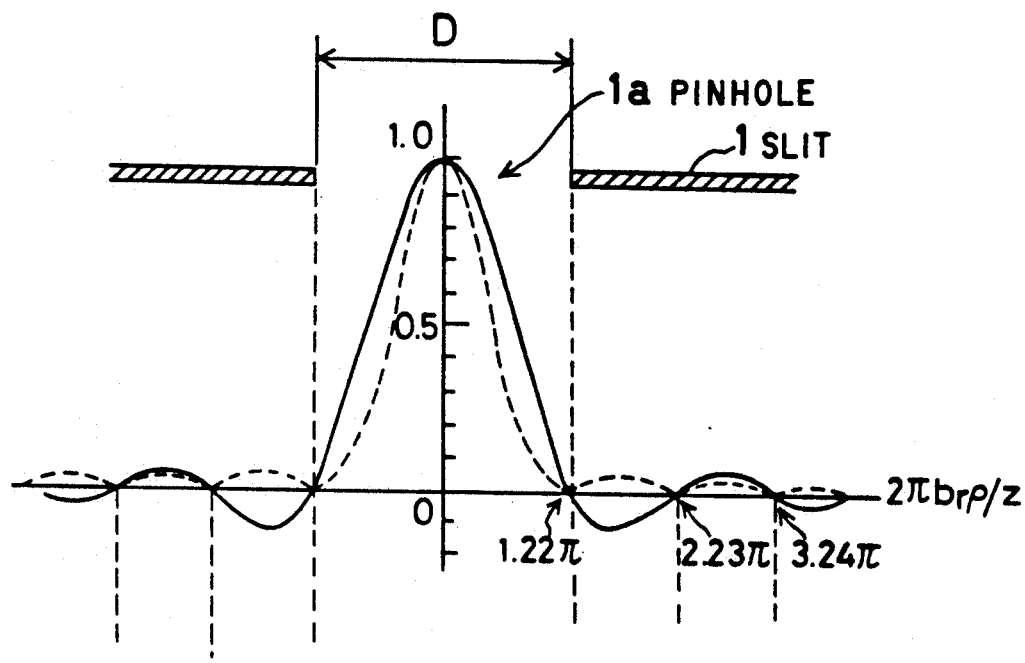
FIG. 10A and 10B are diagrammatic sketches illustrating how to extract the 0 order diffraction image from a Fraunhofer diffraction image.
Figure 10B:
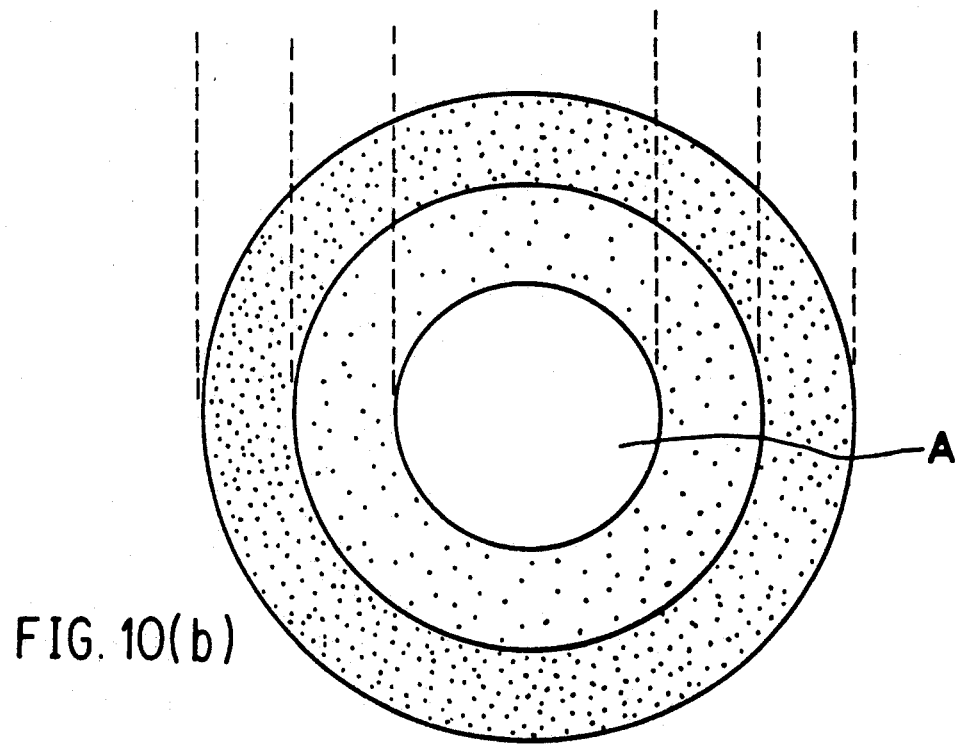

For instance, one of Fraunhofer diffraction images formed through a round aperture is shown in FIGS. 10A and 10B, in which the wave forms shown by solid and broken lines stand for field and light intensities, respectively.

When the round aperture is defined by a pinhole, such a Fraunhofer diffraction image as shown in FIG. 10a is observed at a position sufficiently afar off. As shown in FIG. 10b, this is made up of a plurality of dark rings— called the Airy's disk—and bright zones between the respective dark rings. An inside zone A of the first dark ring or, in a better term, the 0 order spectrum zone, is the brightest of all. Thus, if image observation is made with a slit I whose diameter corresponds to a pinhole diameter equal to n times as large as the width of the 0 order spectrum or which is n times in magnitude as large as a pinhole corresponding to the diameter of the first dark ring, only the 0 order spectrum is then detected as the beat component for heterodyning, thereby removing higher order spectra. If such detection is carried out with respect to the respective points, no interference then occurs at different positions; the van Cittert-Zernike theorem does not hold for image formation. Thus, where scattered light contains minuscule information light as with optical computer tomography, it is possible to separate only the information light from the scattered light for detection. It is here understood that the van Cittert-Zernike theorem holds within a pinhole. According to this invention, however, the zone of which this theorem is true is limited to a spatially resolvable minimum unit.

In the case of a plane wave, the condition for forming a Fraunhofer diffraction image is represented by $$z >> r^2_{max}/2\lambda \quad (12)$$

wherein r is the aperture diameter of a light source and z is the propagation distance. Thus, a Fraunhofer diffraction image may be formed at such a distance as to meet Equation (12) for heterodyning through a pinhole n times as large as the 0 order spectrum thereof.

A Fraunhofer diffraction image formed through a pinhole defined by a round aperture is given by $$I(\rho) = \left(\frac{\pi Dr^2}{\lambda z}\right)^2 \left[\frac{2J_1(2\pi Dr\rho/\lambda z)}{2\pi Dr\rho/\lambda z}\right]^2$$

where Dr is the radius of the pinhole, $J_1$ the Bessel function, $\lambda$ the wavelength and z the optical axis length. The radius of the first dark ring of the Airy's disk is given as follows:

$$\Delta\rho = 0.61 \times z/Dr$$

Contained in the first dark ring is 84% of the total quantity of light. Thus, if this is admitted in the first dark ring defined by the pinhole, detection can then be made at a 16% loss of the plane wave. Since a spherical wave is attenuated in inverse proportion to the square of distance, on the other hand, it is possible to make observation of an image of high resolution by extracting only the 0 order spectrum of the Fraunhofer diffraction image.

Incidentally, achieving extraction of only the 0 order spectrum out of the Fraunhofer diffraction image with a pipe comparable in diameter to the pinhole requires an extremely fine, elongated pipe.

Since the larger the pipe diameter, the smaller the $\Delta\rho$, the use of a normal lens system results in $\Delta\rho$ being extremely reduced in magnitude. Thus, it is difficult to extract only the 0 order spectrum through the pinhole. For this reason, the 0 order spectrum alone is extracted by heterodying with the use of a pinhole larger in magnitude than the 0 order diffraction light. That is to say, the present invention is designed such that a Fraunhofer diffraction image of light obtained by photomixing of laser light transmitted through a sample with light from a local oscillator is observed for the beat component to detect only the 0 order spectrum of the Fraunhofer diffraction image with the use of a relatively short receptor system having a relatively large pinhole diameter.

Figure 1:
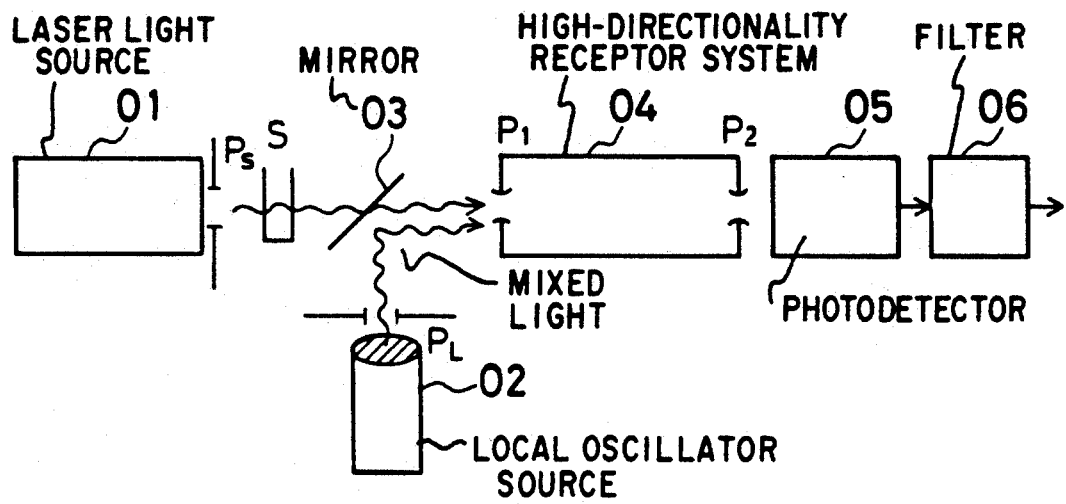
FIG. 1 is a diagrammatic sketch illustrating the construction of the heterodyne receptor system according to this invention.

FIG. 1 is a diagrammatic sketch illustrating the construction of this invention. In this figure, reference numeral 01 stands for a laser light source, S a specimen, 02 a local oscillator source of light, 03 a half mirror, 04 an optical system of high directionality, 05 a photodetector and 06 a filter.

Referring to FIG. 1, the laser light source 01 and the local oscillator source 02 differ in wavelength. Light from the light source 01, which has passed through the sample S, is photomixed with light from the local oscillator source 02, and the resulting light is received by the optical system of high directionality to be described later. The optical system 04, for instance, includes pinholes $P_1$ and $P_2$. The photodetector 05 is used to detect a Fraunhofer diffraction image, and the beat component of light from both the light source 01 and the local oscillator source 02 is detected by the filter 6.

As mentioned below, the amplitude of the signal light of the Fraunhofer diffraction image is determined by whether the aperture is in round, rectangular or annular forms.
Round aperture: $2J_1(X)/X$
Rectangular aperture: $\sin X/X$
Annular aperture: $J_o(X)$
where $J_1$ or $J_0$ is the Bessel function and X is the value determined by what optical system is used.

Figure 2:
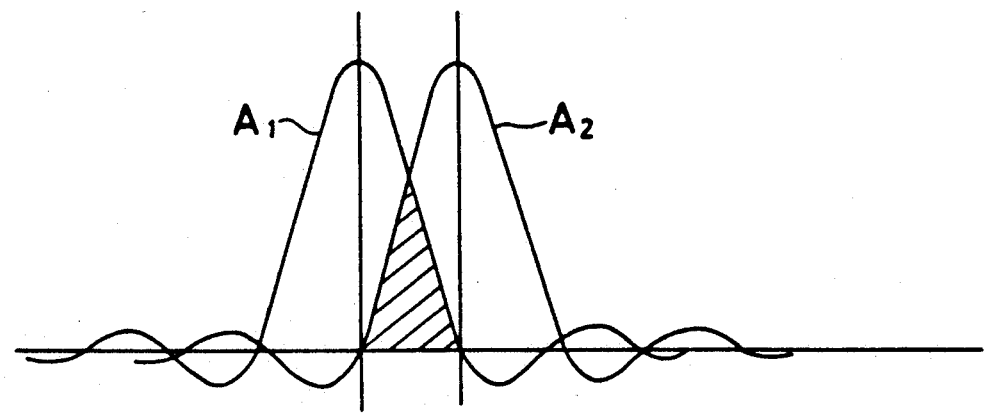
FIG. 2 is a diagrammatic graph illustrating the principle on which heterodyning according to this invention is based.

Assuming that the Fraunhofer diffraction images formed on the light-receiving plane by the light transmitted through the sample and the light from the local oscillator source are expressed in terms of $A_1$ and $A_2$ in FIG. 2, then the beat component detected through the filter 06 is defined by a hatched region therein. Since the beat component is detected as the product of the Fraunhofer images $A_1$ and $A_2$, it is corresponding to the area of the overlapping regions of the 0 order spectra. This area reaches a maximum when $A_1$ and $A_2$ are in agreement with each other, and decreases as the amount of overlapping decreases. Thus, even when the diameter of the pinhole is sufficiently large to extract a diffraction image at most n times in magnitude as large as the 0 order spectrum, any higher order component cannot be detected because the signals detected are made up of the beat component. The signal intensity of this beat component, which varies depending upon a combination of the aperture geometries for the received light and the light from the local oscillator, is determined in the form of the product of both the amplitudes, as shown in FIG. 3, and reaches a maximum when the aperture geometry for the received light coincides with that for the light from the local oscillator. For heterodyning, it is thus preferred that both the apertures coincide with each other in geometry. However, this is a matter of choice that is determined by the purpose for which measurement is made.

FIGS. 11 to 15 illustrate an optical system of high directionality, which serves as a receptor element for selecting a diffraction image n times in magnitude as large as the 0 order spectrum of a Fraunhofer diffraction image at the exit end thereof.

Figure 11:
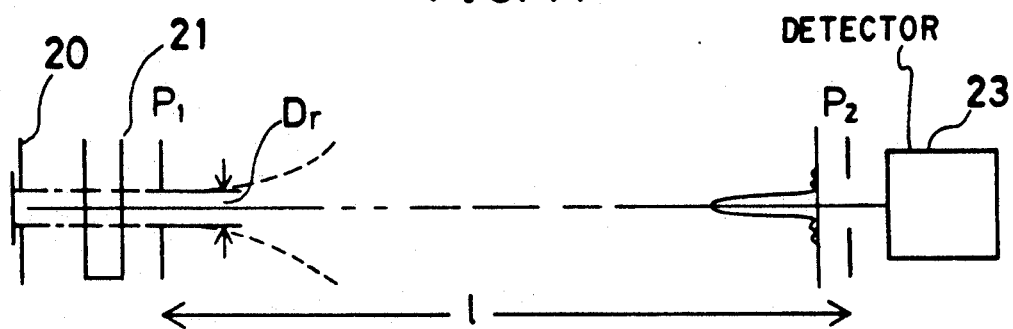
FIG. 11 is a diagrammatic sketch illustrating an optical system for detecting the 0 order spectrum by two pinholes.

FIG. 11 illustrates one embodiment of the high-directionality optical system having an aperture according to this invention, which serves as a receptor element for detecting a diffraction image.

Laser light is directed from a light source 20 onto a sample 21, the transmitted light from which is passed through a slit $P_1$ and thence through a slit $P_2$ spaced away from it by such a distance l as to satisfy Equation (12), to detect the 0 order light by a detector 23.

Now let us assume that the pinhole diameter D of the slit $P_2$ can be represented as the following relation:

$$D = 2\Delta\rho = 1.22 \times \lambda l/Dr \qquad (13)$$

wherein Dr is the pinhole diameter of the slit $P_1$, $\lambda$ is the wavelength of the laser light and $\Delta\rho$ is the radius of a first dark ring. If $\lambda = 500$ nm, $l = 6$ m and $Dr = 1$ mm, then $D = 7.32$ mm. With the heterodyning receptor system of this invention wherein any higher order component cannot be detected even when a diffraction image at most n times as large as the 0 order spectrum is being extracted, however, the pinhole diameter D may be several times as large as that value.

Figure 12:
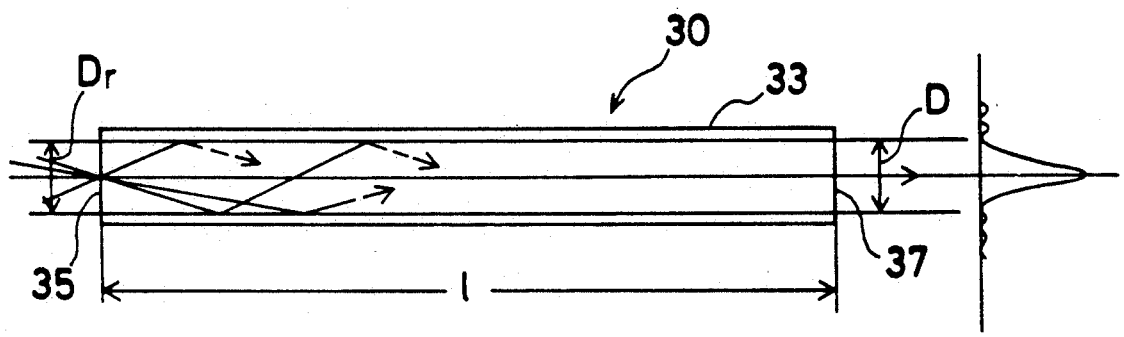
FIG. 12 is a diagrammatic sketch illustrating a high-directionality optical system, the inner surface of which is coated with an absorber.

FIG. 12 is a diagrammatic sketch illustrating another embodiment of the high-directionality optical system, wherein reference numeral 30 stands for an optical element of high directionality, 33 a light absorber, 35 a core and 37 a cladding.

Referring to this figure, the optical element 30, for instance, may be formed of a linear, elongated, hollow glass fiber, the inner wall of which is coated with such a light absorber as carbon.

Upon incidence of light from an entrance plane 35, a light beam parallel with the optical axis of the optical element 30 propagates rectilinearly and leaves an exit plane 37. However, a light beam at an angle with the optical axis is unlikely to leave the plane 37, because it has impinged upon the wall face and been absorbed therein. Now assuming that D is the aperture diameter of the optical element 30, l is the length of the optical element 30 and $\lambda$ is the wavelength of incident light. Then the relation $l \alpha Dr^2/\lambda$ holds for the length l, as detected, of a Fraunhofer diffraction image formed on the plane 37 with perfect plane waves, since the components at angles with the optical axis have been absorbed. This length enables the Fraunhofer diffraction image to be viewed.

Now consider incident light having a wavelength of 6328 angstroms by way of example. If $Dr = 10$ mm, then $l = 600$ m; if $Dr = 0.01$ mm, then $l = 0.6$ m; if $Dr = 0.1$ mm, then $l = 6$ cm; if $Dr = 0.01$ mm, then $l = 0.6$ mm; if $Dr = 1$ μm, then $l = 6$ μm; and if $Dr = 0.5$ gm, then $l = 1.25$ μm.

Thus, if the aperture diameter and length of the high-directionality optical element are preset depending upon the object to be measured and that length is sufficiently long relative to that aperture diameter, then it is possible to extract only plane waves parallel with the optical axis from light waves entering the optical element, In order to achieve substantial plane wave propagation, however, it is required that the diameter of the optical element be larger than the wavelength of incident light. If the optical element should have a diameter nearly equal to the wavelength of incident light, so large would the amount of diffraction be that the quantity of light extracted is extremely reduced. In this embodiment, the optical element can also be increased in diameter by using the heterodyne receptor system.

When the plane waves as signal light are detected in the form of the 0 order Fraunhofer diffraction image alone, the degree of separation of incoherent scattered light from plane waves is given by (Scattering Intensity)/(Intensity of Transmitted Plane $$\text{Waves}) = (\lambda/D_r)^2$$

wherein $D_r$ is the diameter of the entrance aperture of the highly directional optical element and $\lambda$ is the wavelength.

In other words, the larger is the aperture diameter $D_r$ relative to the wavelength, the more the attenuation of scattered light, so that it can be separated from the plane waves. Even when a Fraunhofer diffraction image n times as large as the 0 order spectrum is detected through the pinhole, the separating power is on the same level, because the beat component is of the same zero order as mentioned above.

In a modification to FIG. 12 that is contrary to a conventional optical fiber, the index of refraction of the core section is made smaller than that of the rest. Light beams at angles with the optical axis dissipate without being subjected to total reflection. Even through a part of them is reflected, all this comes to disappear from the optical element while reflection is repeated several times. It is thus possible to detect all plane waves but scattered components.

Figure 13:
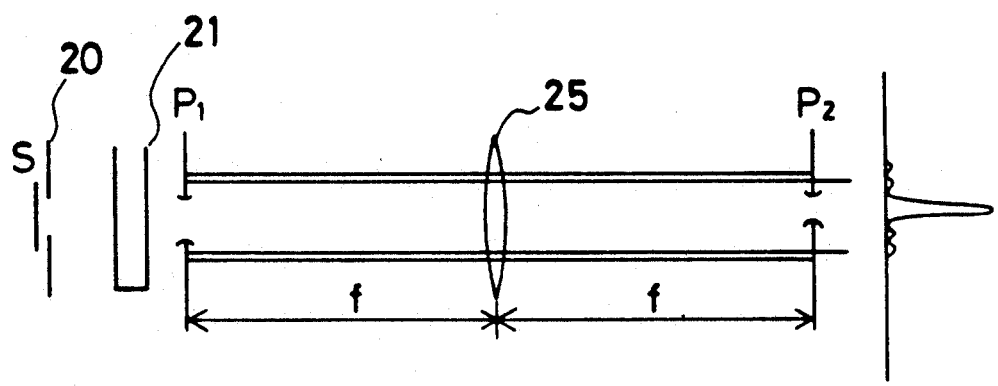
FIG. 13 is a diagrammatic sketch illustrating one embodiment of this invention, wherein the 0 order spectrum is detected by a long-focus lens.

FIG. 13 is a diagrammatic sketch illustrating a further embodiment of this invention, in which a lens is used.

Referring to FIG. 13, a lens 25 is used to form a Fraunhofer diffraction image through an aperture on the front focal plane and focus it onto the back focal plane, whereby the length of a receptor system can be reduced. In this lens system, the aperture diameter D may again be found by Equation (13). Now consider incident light having a wavelength of 500 nm by way of example. If the focal length $f = 1$ m and $D_r = 1$ mm, then $D = 1.22$ mm, or if the focal length $f = 5$ m and $D_r = 5$ mm, then $D = 1.22$ mm. The use of this embodiment in combination with heterdyning according to this invention enables the length of the receptor system to be further reduced.

Figure 14:
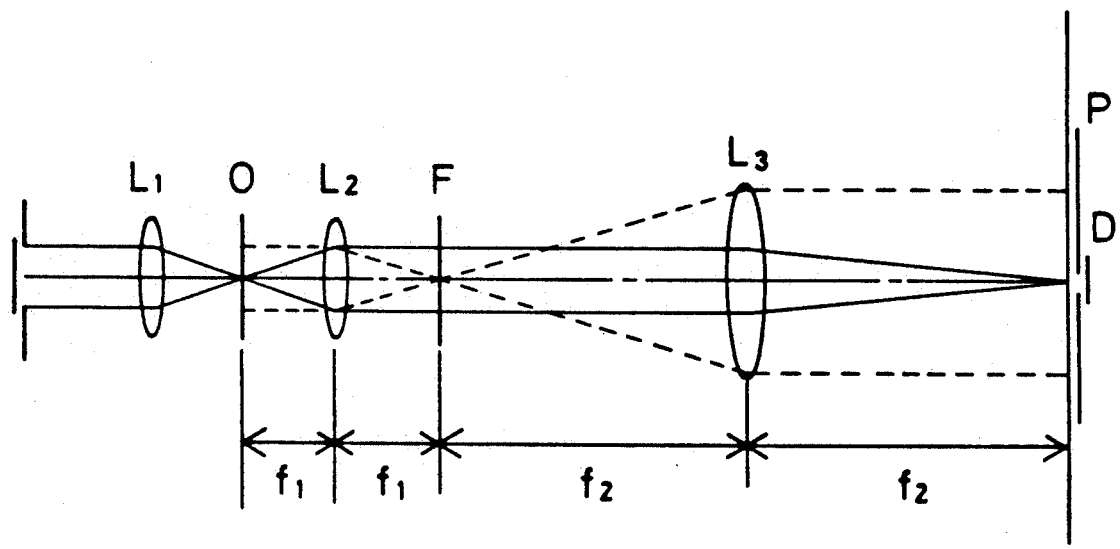
FIG. 14 is a diagrammatic sketch illustrating an embodiment of a microscopic optical system for optical CT.

FIG. 14 is a diagrammatic sketch illustrating an embodiment of the microscopic optical system for optical computer tomography.

Referring to FIG. 14, laser light is converged through a condenser lens $L_1$ onto a sample 0. The sample is then located in the vicinity of the front focal point of an objective $L_2$ for observation on an enlarged scale. In this case, the Fraunhofer diffraction image of the sample 0 is formed through the objective $L_2$ on the back focal point F. The size of the resulting 0 order diffraction image is then considered tantamount to a Fraunhofer diffraction image formed through the objective $L_2$ when plane waves enter an aperture equal in size to the 0 order diffraction image on the focal plane of the condenser lens $L_1$ (which is found within the sample plane). However, this is true when the size of the 0 order spectrum of the Fraunhofer diffraction image formed on the focal plane of the objective $L_2$ upon incidence of plane waves on it satisfies the condition that it must be larger than that of the 0 order spectrum of the Fraunhofer diffraction image formed through the condenser lens $L_1$.

At this time, the size of the 0 order diffraction image exceeds the order of millimeter. Thus, the incoming light is brought in wavefront alignment with light from a local oscillator on the focal plane or a position before or after it, where heterodyning takes place. Alternatively, a reduced image that is the Fourier transformation image of the 0 order diffraction image is formed on the focal plane through an eyepiece $L_3$, which is extracted through a pinhole P for heterodyning. The size D of the 0 order diffraction image on this pinhole becomes $$D \approx \lambda f_2/D_2$$

wherein $f_2$ and $D_2$ are the focal length and aperture of the eyepiece $L_3$, respectively. Thus, D may be made smaller or larger than the size of the 0 order diffraction image on the plane 0 of the sample by selecting the F value of the lens $L_3$-$f_2/D_2$. In order to view a general image of the sample with this embodiment, the sample's plane may be scanned with laser light. In FIG. 14, broken lines represent optical paths for scattered light, which diffuses in the form of spherical waves and is attenuated.

Figure 15:
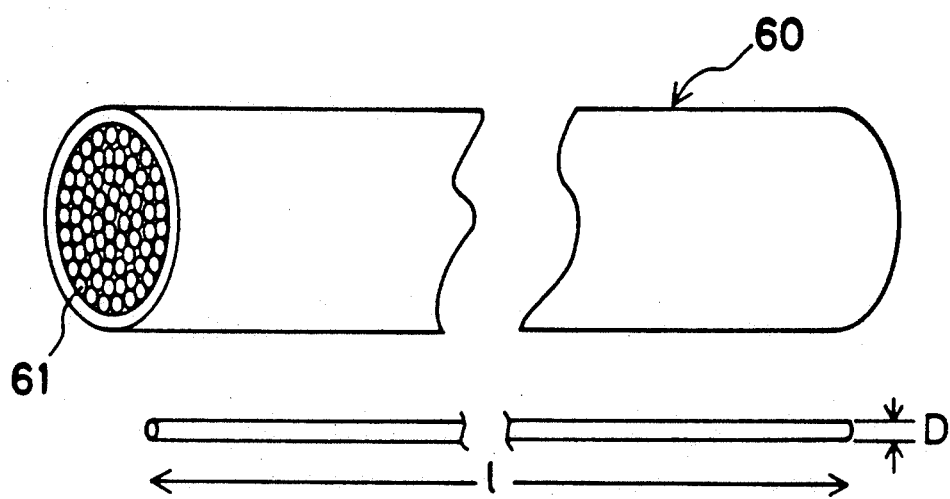
FIG. 15 is a diagrammatic sketch illustrating an embodiment of an optical system of high directionality wherein a bundle of a plurality of optical units according to this invention is used.

FIG. 15 is a diagrammatic sketch illustrating an embodiment of the high-resolution optical system comprising a bundle of a plurality of the optical systems of high directionality according to this invention, with which a general image of a sample can be viewed at once.

An optical unit 60, for instance, is built of a plurality of such optical elements 61 as described in connection with FIGS. 11 to 14, and has such a length 1 as to satisfy Equation (12). The aperture D of this unit is such that a diffraction image at most n times as large as the 0 order spectrum is extractable from Fraunhofer diffraction images. By using such an optical unit in combination with heterodyning, it is possible to view a clear object image because at the exit end of the optical unit, the optical elements are independent of each other with no interference in the respective positions.

Figure 16:
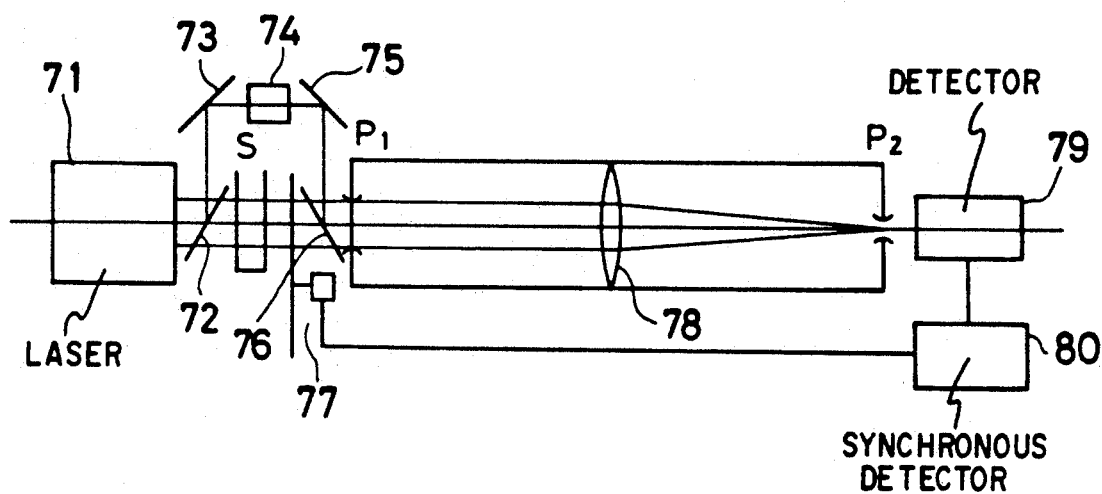
FIG. 16 is a diagrammatic sketch illustrating the heterodyning system using a long-focus lens according to this invention.

FIG. 16 is a diagrammatic sketch illustrating an embodiment of the high-directionality optical system comprising a lens and pinholes, which is used in combination with heterodyning.

Referring to FIG. 16, light form a laser light source 71 is divided by a half mirror into two portions. One light portion is directed onto a sample S, while the other is photomixed with the light transmitted through the sample S by way of a mirror 73, a phase shifter 74 and a mirror 75. The light passing through the phase shifter 74 has its frequency shifted, and photomixed with the rectilinearly propagating light, entering a receptor system through an aperture $P_1$. A long-focus lens 78 has its front focal plane located at the aperture position, and a Fraunhofer diffraction image formed through the aperture is extracted through a pinhole P2 located on the back focal plane of the long-focus lens, the beat component of which is in turn detected by a detector 79. Detection of the beat component is synchronized with the operating cycle of a chopper 77, thereby removing such gradual variations as power or temperature variations. And the use of the long-focus lens enables the length of the receptor to be reduced.

Figure 17:
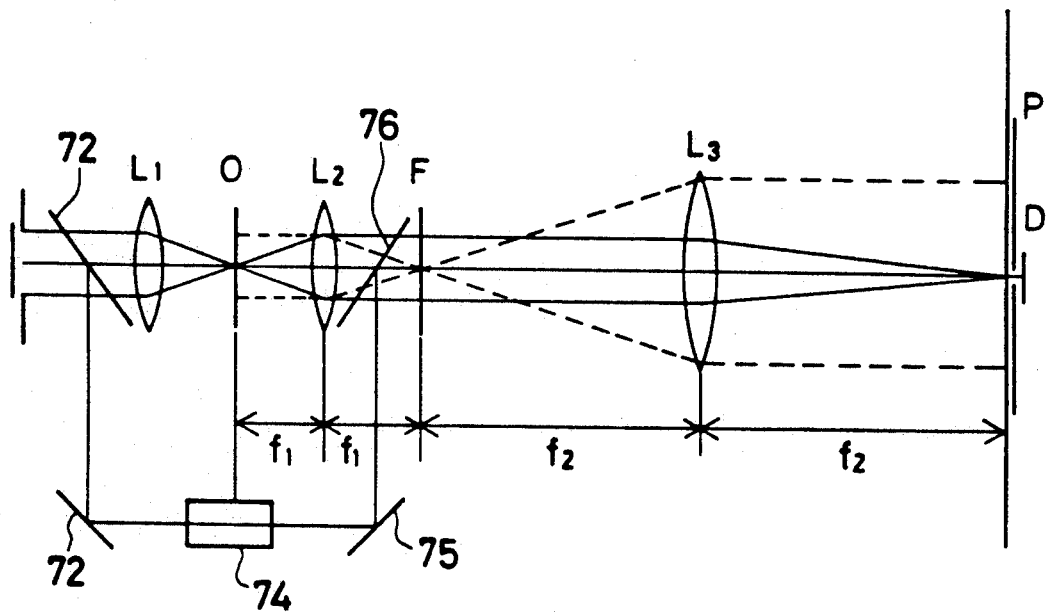
FIGS. 17 and 18 are diagrammatic sketches illustrating heterodyning with a microscopic optical system for optical CT.

FIG. 17 is a diagrammatic sketch illustrating an embodiment of the microscopic optical system for optical computer tomography.

Referring to FIG. 17, laser light is split into two laser beams by a half mirror. One laser beam is converged through a condenser lens $L_1$ onto a sample 0 placed in the vicinity of the front focus of an objective $L_2$, while the other laser beam is frequency-shifted by a phase shifter and photomixed on a half mirror 76 with the light from the objective. Then, the resulting image is then enlarged through an eyepiece $L_3$ whose front focus is located at the back focus position of the objective $L_2$, with its beat component being detected through a pinhole in a plane P. Now let us assume that $f_1$ and $f_2$ represent the focal lengths of the objective and eyepiece, respectively. Then, the Fraunhofer diffraction image observed satisfies the relation $f_2 > f_1$. In order to observe a general image of the sample with this embodiment, the sample's plane may be scanned with laser light.

Figure 18:
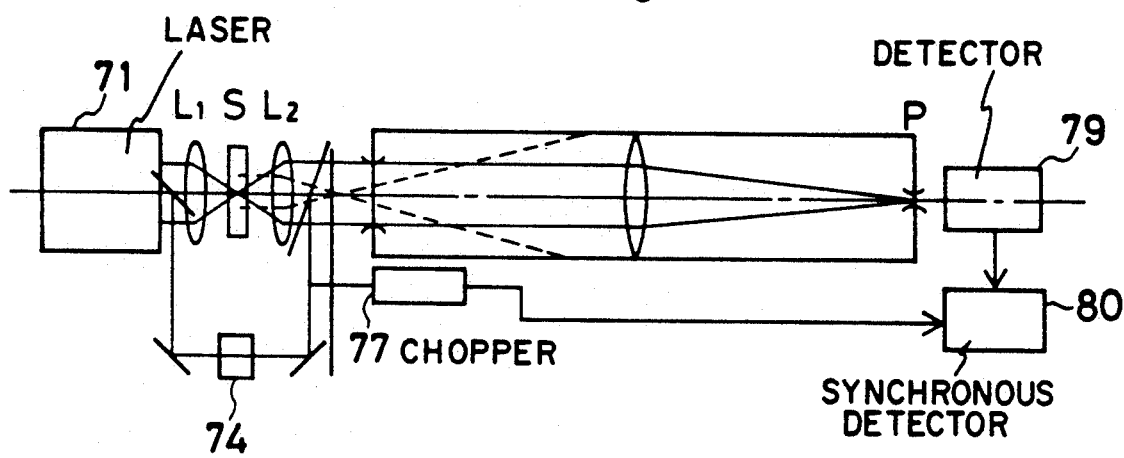

FIG. 18 is a diagrammatic sketch illustrating another embodiment of the microscopic optical system for optical computer tomography.

This embodiment is similar to that of FIG. 17 with the exception that the mixed light is intermitted by a: chopper 77 and detection of the beat component is synchronized with an intermittence cycle.

Figure 19:
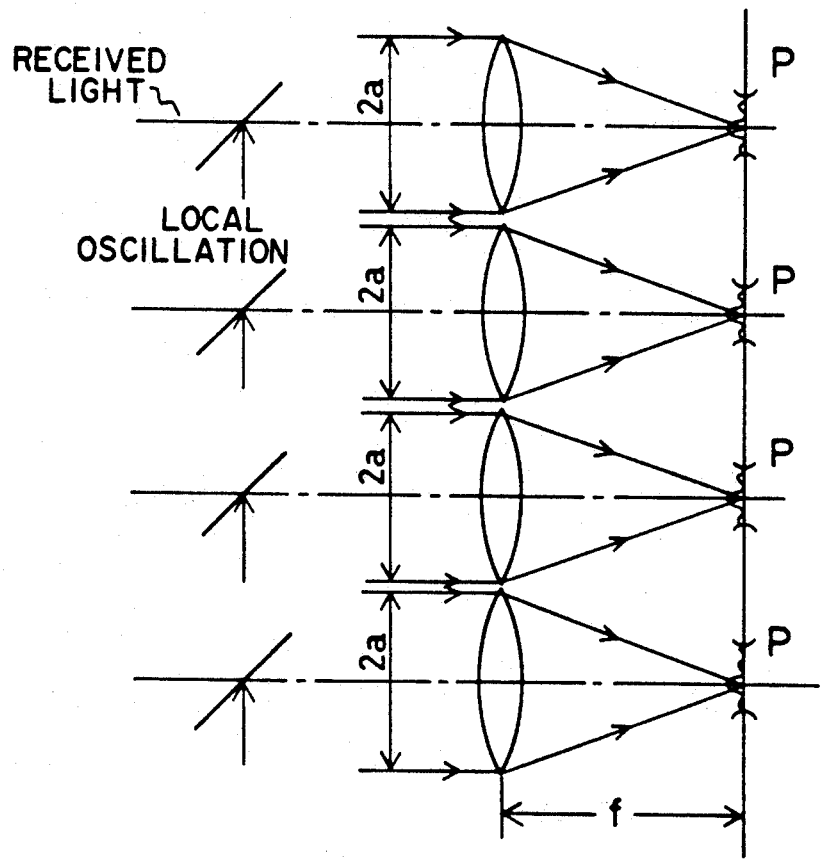
FIG. 19 is a diagrammatic sketch illustrating an embodiment wherein heterodyning is carried out with a bundle of a plurality of long-focus lens receptor systems.

Referring to FIG. 19, there is shown an embodiment of the optical unit made up of a bundle of a plurality of optical elements, each having a lens, on the focal plane of which a Fraunhofer diffraction is formed, thereby reducing the length of the optical system. Photomixed light of received light with local oscillation light is allowed to enter each of the optical elements. It is thus possible to detect the beat component with a relatively short optical system and obtain an optical tomogram of high resolution.

Figure 20:
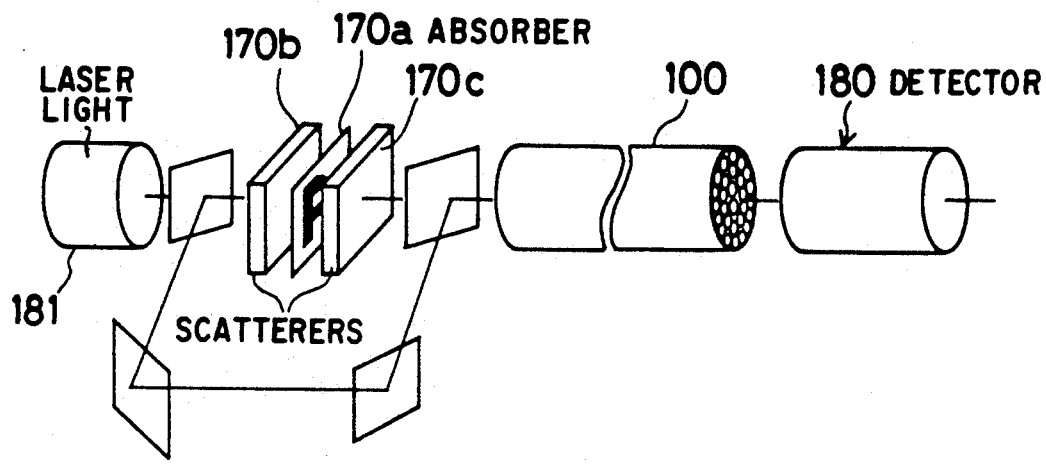
FIG. 20 is a conceptional sketch illustrating how to observe an image by heterodyning.

FIG. 20 is a diagrammatic sketch illustrating an embodiment wherein an image of such an object as a living body is observed with the heterodyning and high-directionality optical system according to this invention.

Light from a laser light source 181 is divided by a half mirror into two laser beams. One laser beam is directed onto an absorber 170a buried between scatterers 170b and 170c, while the other laser beam is frequency-shifted through a phase shifter for photomixing with the transmitted beam. The resulting beam is directed through a high-directionality optical system 100 built of a bundle of a plurality of receptor elements according to this invention, and the beat component of the formed Fraunhofer diffraction image is detected by a detector 280. With such an arrangement, it is possible to observe an optical tomogram of the human body or the like with high resolution.

Figure 21:
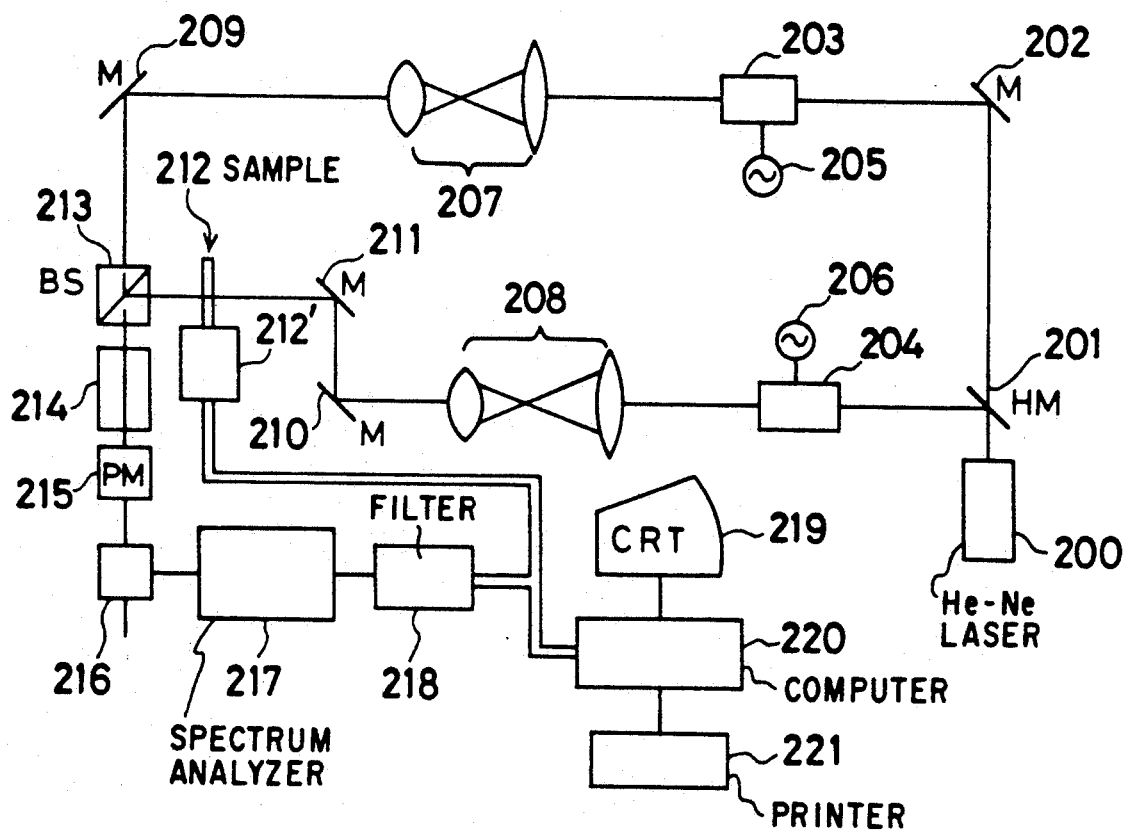
FIG. 21 is a diagrammatic sketch illustrating an embodiment of the arrangement for imaging optical tomograms using heterodyning according to this invention, FIGS. 22 and 23 each are a diagrammatic sketch illustrating conventional methods of observing optical computer tomograms.
Figure 22:
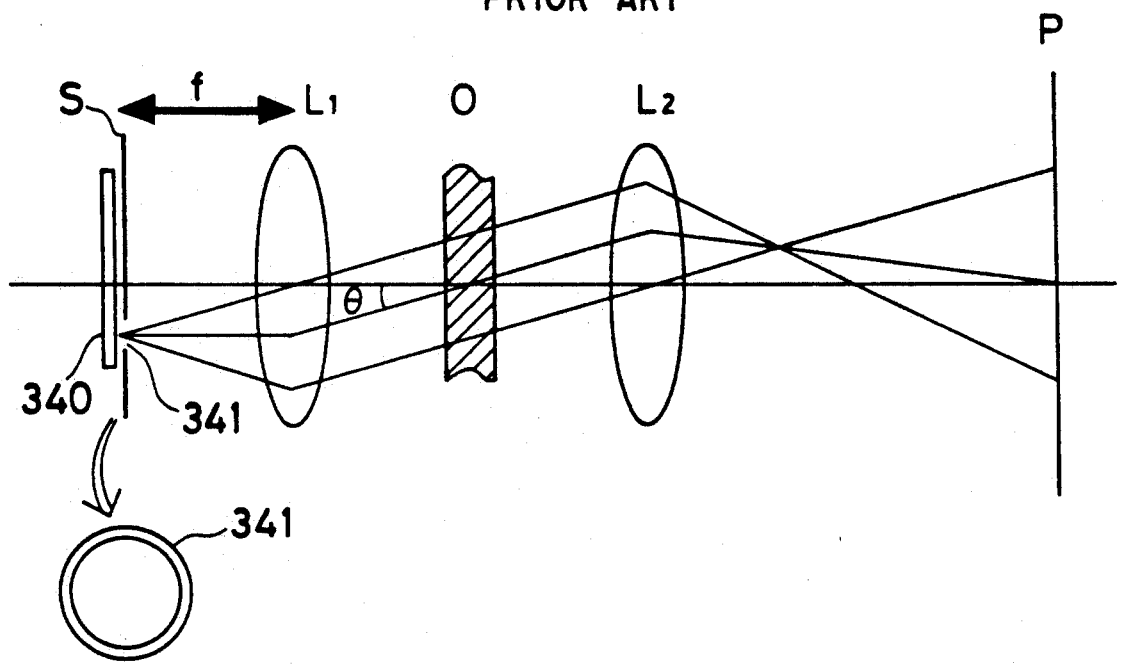
Figure 23:
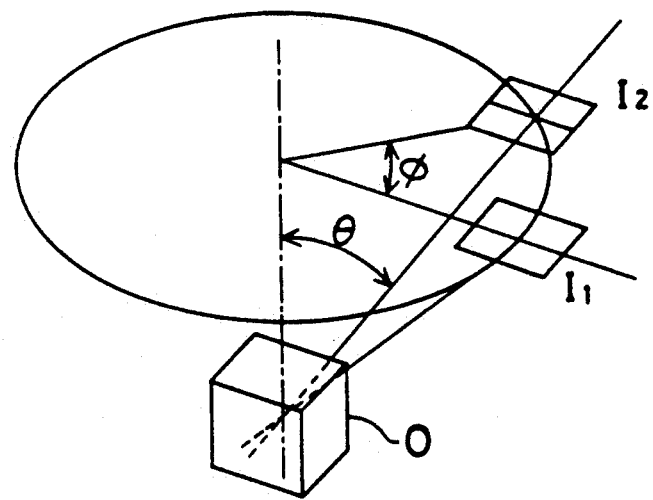
Figure 24:
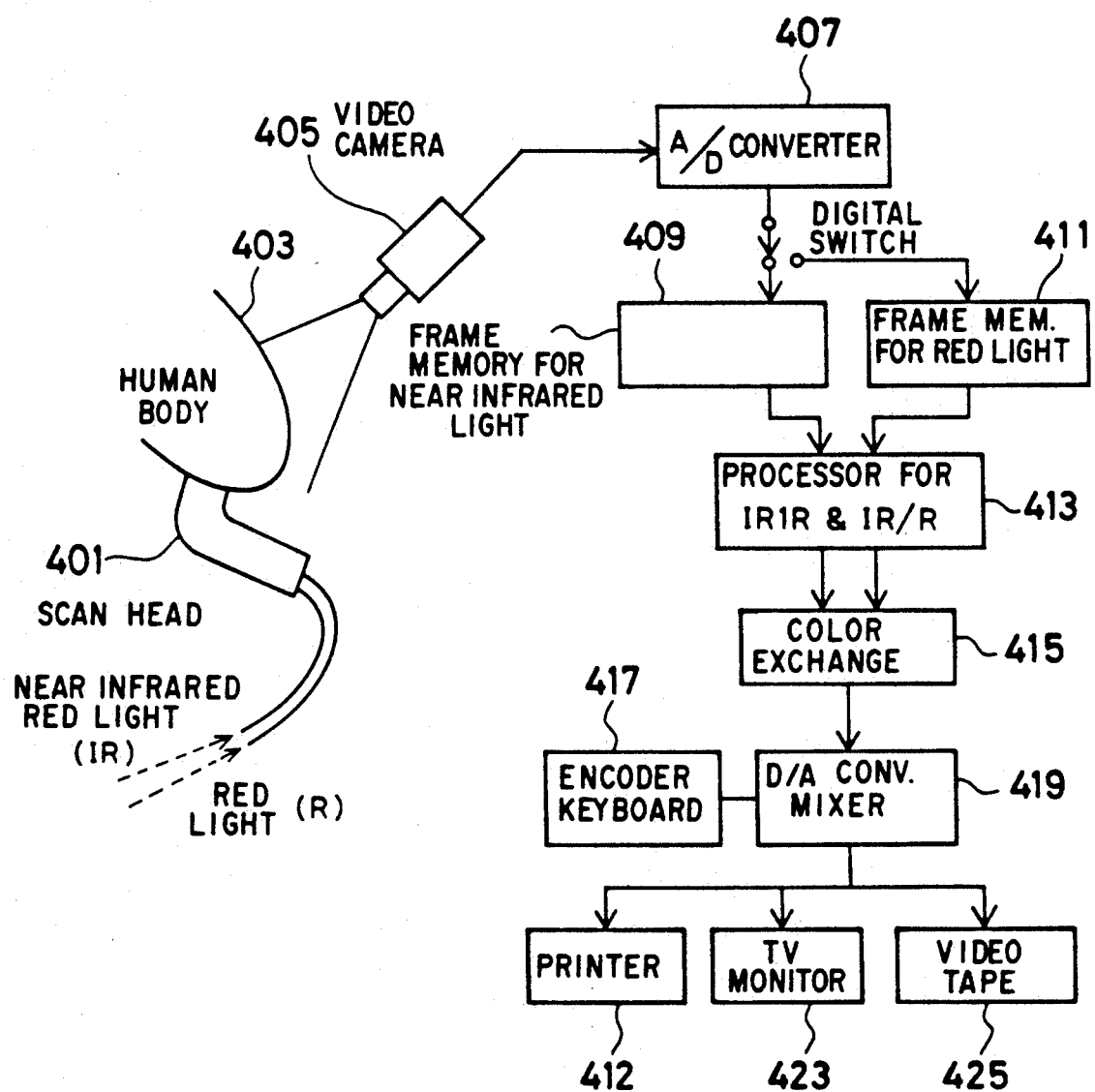
FIG. 24 is a diagrammatic sketch illustrating the construction of conventional equipment for obtaining a light absorption distribution image.
Figure 25:
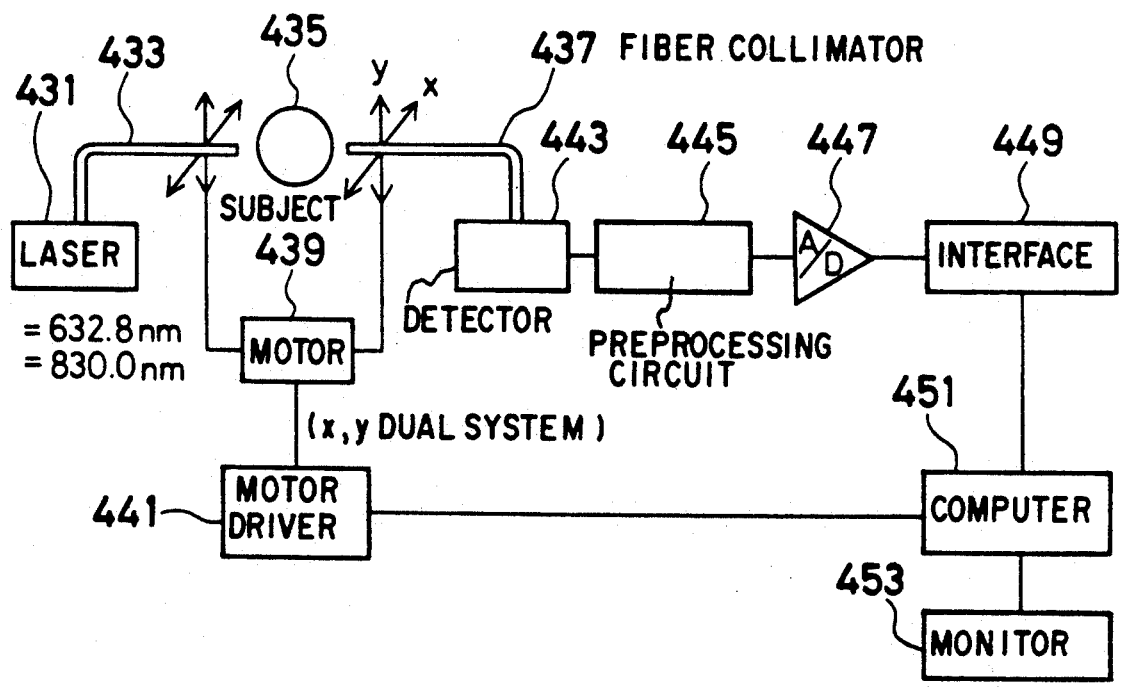
FIG. 25 is a diagrammatic sketch illustrating the construction of another conventional equipment for obtaining a light absorption distribution image.
Figure 26:
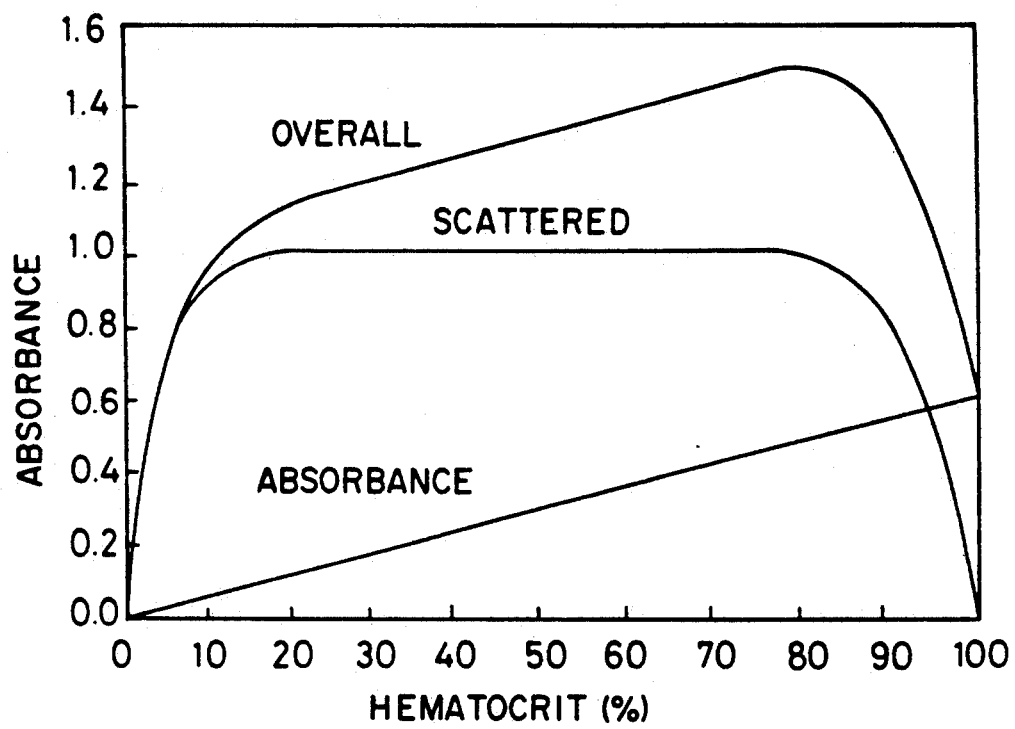
FIG. 26 is a diagrammatic graph showing the Twersky's scattering theory curves.
Figure 27:
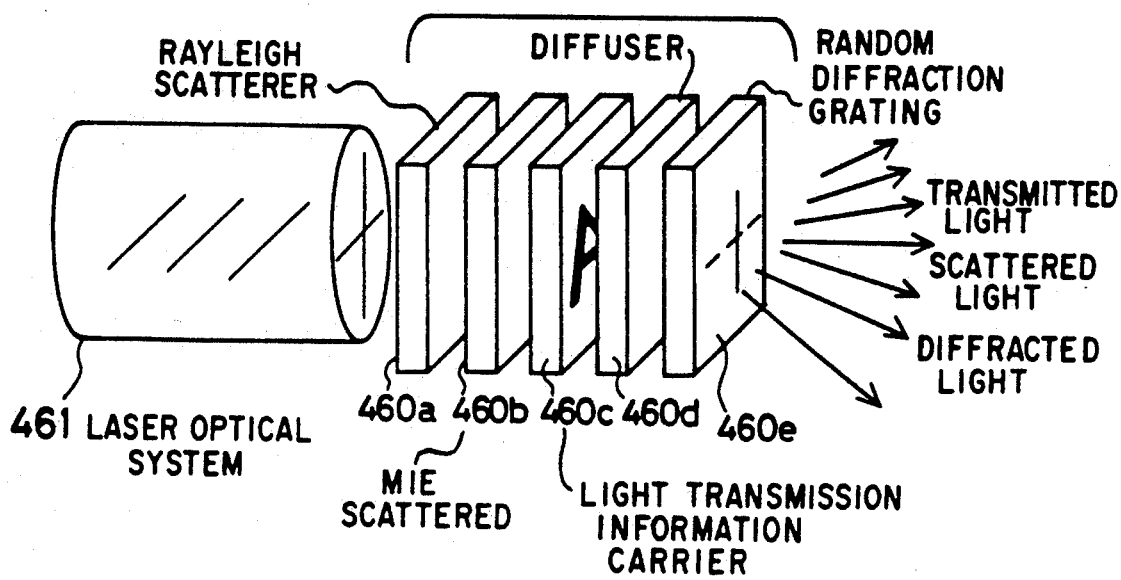
FIG. 27 is a diagrammatic illustration of optical properties of a living body.
Figure 28:
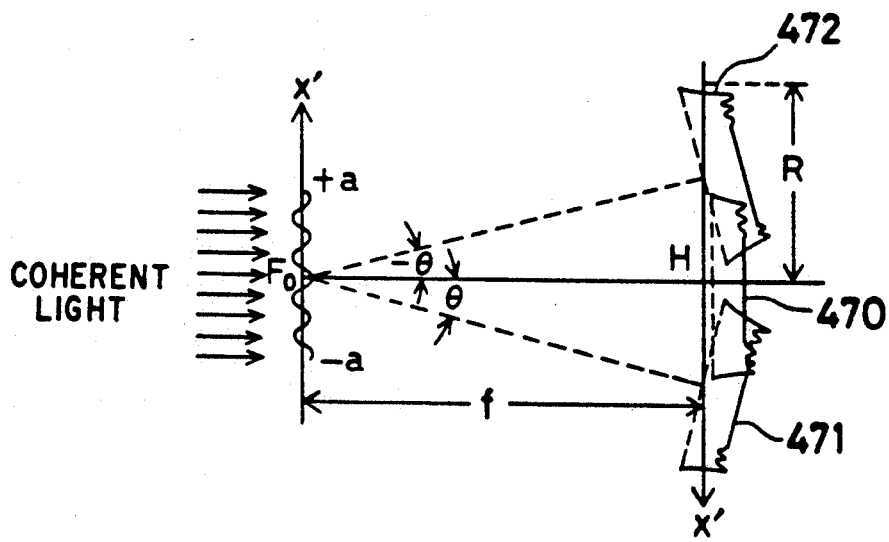
FIG. 28 is a diagrammatic sketch illustrating a diffraction pattern produced through a finite aperture.
Figure 29A:
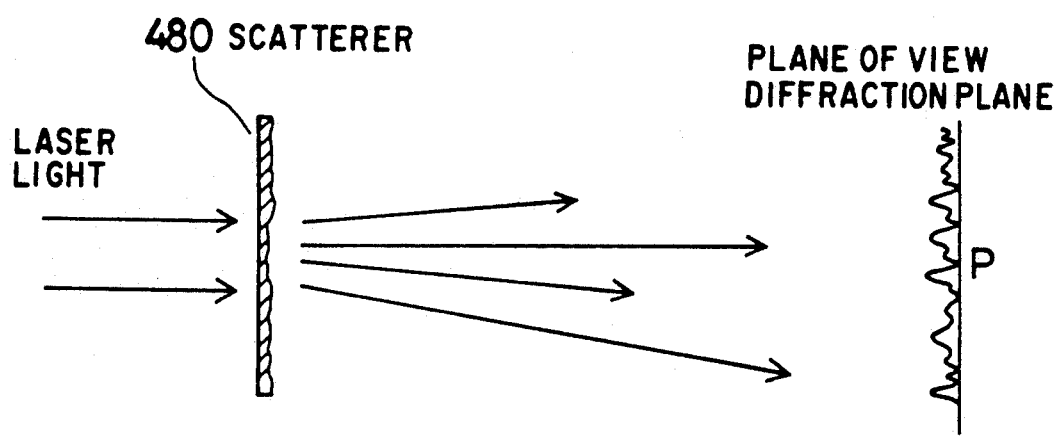
FIGS. 29A and 29B are diagrammatic sketches illustrating random diffraction patterns produced through a scatterer.
Figure 29B:
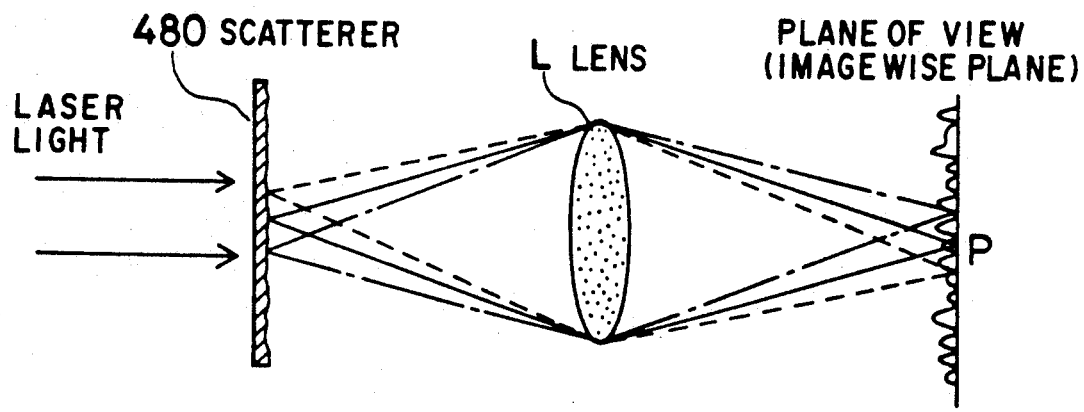

FIG. 21 is a diagrammatic sketch illustrating one embodiment of the arrangement for imaging optical tomograms, in which the optical system of this invention is incorporated.

Laser light from an He-Ne laser 200 is divided by a half mirror 201 into two laser beams, which are then frequency-modulated by acoustooptic modulators 203 and 204 driven by modulators 205 and 206 to make a frequency difference f between them. Then, a beam leaving the modulator 204 is directed through an objective 208 onto a sample 212 driving by a pulse stage 212'. The transmitted beam is photomixed with a beam passing through an objective 207 and a mirror 209 by a beam splitter 213, entering a high-directionality optical system 214, whence it is processed in a receptor 215, amplified by an amplifier 216 and spectrum-analyzed in a spectral analyzer 217 and processed through a filter 218 having a zone f to detect the beat component. The beat component bears information about a transmission image buried in the scattered components. While the sample is moved by the pulse stage 212', the beat component is detected and image-processed in a computer 200 to display an optical tomogram on a CRT 219. If required, this image is printed out with a printer 221.

According to this invention as mentioned above, signal light and local oscillation light are photomixed together, and the beat component of the resulting light is detected, whereby any higher order component can be cut off, even when a spectrum n times as large as the 0 order spectrum is extracted out of Fraunhofer diffraction images. In other words, since it is difficult to extract the 0 order Fraunhofer diffraction image alone due to its too small a size, heterodyning is used with a pinhole having an increased diameter, thereby fixing the aperture of the receptor system at a practical value.

INDUSTRIAL APPLICABILITY

The present invention, according to which only information light can be picked out of scattered components as mentioned above, is applicable to optical computer tomography, etc. If this invention is applied to the human body or the like, it is then possible to view only a vascular image of the human body by using a wavelength corresponding to the absorption region of hemoglobin, to make observation of an image of a nervous system by using light at a wavelength corresponding to the absorption wavelength of the nervous system, or to make clear images of specific cells having a given absorption wavelength such as cerebral or bone cells by illuminating them with light having that absorption wavelength. Thus, this invention makes breakthroughs in medical or like other techniques.

What is claimed is:

1. A heterodyning receptor system, comprising:
   a first laser light source supplying a first laser light transmitted through a sample;
   a second laser light source supplying a second laser light having a frequency different from that of said laser light produced by said first laser light source;
   photomixing means for photomixing said first laser light transmitted through the sample with said second laser light;
   a receptor element which the resulting light enters and divides a light propagating zone into a plurality of sub-zones; and
   a detector means for detecting a beat component of the resulting photomixed light out of light leaving said receptor element;
   said receptor element having an exit end, at which a spatial zone, which is defined between different points and in which interference occurs, is limited within a spatially resolvable minimum unit to detect the beat component of the photo mixed light.

2. A receptor system as claimed in claim 1, wherein said spatially resolvable minimum unit is limited by detecting a diffraction image at most n times as large as the 0 order spectrum of a Fraunhofer diffraction image, where n is an integer greater than 1, at the exit end of said receptor element.

3. A receptor system as claimed in claim 1, wherein said receptor element detects the whole or a part of the 0 order diffraction image of a Fraunhofer diffraction image at the exit end of said receptor element.

4. A receptor system as claimed in any one of claims 1 to 3, wherein said receptor element is made up of an elongated pipe having pinholes at its entrance and exit ends.

5. A receptor system as claimed in any one of claims 1 to 3, wherein said receptor element is made up of a hollow, elongated pipe coated on its wall face with a light absorbing material.

6. A receptor system as claimed in any one of claims 1 to 3, wherein said receptor element is made up of a straight optical fiber having a longitudinal axis, a core portion and a clad portion, said core portion having a smaller index of refraction than said clad portion, such that light entering said optical fiber at an angle less than a particular angle to the axis of said optical fiber is transmitted along said optical fiber and all other light is entering said optical fiber is scattered out of said core portion.

7. A receptor system as claimed in any one of claims 1 to 3, wherein said receptor element includes a long-focus lens whose front and back focuses are located at its entrance and exit ends, respectively.

8. A receptor system as claimed in any one of claims 1 to 3, wherein said receptor element includes an objective whose front focal position is located at said sample and an eyepiece whose front focal position is located at the back focal position of said objective.

9. An arrangement for visualizing optical transmission images, characterized by including a stage for moving a sample, means for directing one of two laser beams with a given frequency difference therebetween onto said sample and photomixing the transmitted light with the other laser beam, a receptor element which the resulting light enters and divides a light propagating zone into a plurality of sub-zones, said receptor element having an exit end, at which a spatial zone, which is defined between different points and in which interference occurs, is limited within a spatially resolvable minimum unit, and a detector for detecting a beat component of the mixed light out of light leaving said receptor element, means for computing the detected signals, and means for displaying the result of said computing, whereby a beat component is extracted from light leaving said sample to visualize an optical transmission image.

10. An arrangement for visualizing optical transmission images as claimed in claim 9, characterized in that said spatially resolvable minimum unit is limited by detecting a diffraction image at most n times as large as the 0 order spectrum of a Fraunhofer diffraction image at the exit end of said receptor element.

11. An arrangement for visualizing optical transmission images as claimed in claim 9, wherein said spatially resolvable minimum unit is limited by detecting a diffraction image at most n times as large as the 0 order spectrum of a Fraunhofer diffraction image, where n is an integer greater than 1, at the exit end of said receptor element.

12. An arrangement for visualizing optical transmission images, comprising:

a stage for moving a sample;

means for directing one of two laser beams with a given frequency difference therebetween onto said sample and photomixing the transmitted light with the other laser beam;

a receptor element which the resulting light enters and divides a light propagating zone into a plurality of sub-zones; said receptor element having an exit end, at which a spatial zone, which is defined between different points and in which interference occurs, is limited within a spatially resolvable minimum unit;

a detector for detecting a beat component of the mixed light out of light leaving said receptor element;

means for computing the detected signals; and means for displaying the result of said computing;

whereby a beat component is extracted from light leaving said sample to produce a visible optical transmission image.

* * * * *